(12) United States Patent
Vaya et al.

(10) Patent No.: US 11,591,288 B2
(45) Date of Patent: Feb. 28, 2023

(54) COMPOSITIONS AND METHODS FOR TREATING ATHEROSCLEROTIC CARDIOVASCULAR DISEASE

(71) Applicant: GAVISH-GALILEE BIO APPLICATIONS LTD., Kiryat Shmona (IL)

(72) Inventors: Jacob Vaya, Mitzpe Amouka (IL); Soliman Khatib, Ghajar (IL); Emma Kvitnitsky, Kiryat Shmona (IL)

(73) Assignee: GAVISH-GALILEE BIO APPLICATIONS LTD., Kiryat Shmona (IL)

( * ) Notice: Subject to any disclaimer, the term of this patent is extended or adjusted under 35 U.S.C. 154(b) by 322 days.

(21) Appl. No.: 16/641,242

(22) PCT Filed: Aug. 22, 2018

(86) PCT No.: PCT/IL2018/050924
§ 371 (c)(1),
(2) Date: Feb. 23, 2020

(87) PCT Pub. No.: WO2019/038764
PCT Pub. Date: Feb. 28, 2019

(65) Prior Publication Data
US 2020/0308100 A1    Oct. 1, 2020

Related U.S. Application Data

(60) Provisional application No. 62/621,261, filed on Jan. 24, 2018, provisional application No. 62/549,058, filed on Aug. 23, 2017.

(51) Int. Cl.
*C07C 229/22* (2006.01)
*A61P 9/10* (2006.01)
*A61P 3/06* (2006.01)

(52) U.S. Cl.
CPC .............. *C07C 229/22* (2013.01); *A61P 3/06* (2018.01); *A61P 9/10* (2018.01)

(58) Field of Classification Search
CPC .................................................. C07C 229/22
See application file for complete search history.

(56) References Cited

U.S. PATENT DOCUMENTS

| | | | |
|---|---|---|---|
| 4,478,734 A * | 10/1984 | Ogino | A61Q 5/02 510/237 |
| 5,753,703 A | 5/1998 | Cavazza et al. | |
| 6,180,680 B1 | 1/2001 | Cavazza | |
| 9,315,838 B2 | 4/2016 | Benning et al. | |
| 2012/0214870 A1 | 8/2012 | Evans et al. | |

FOREIGN PATENT DOCUMENTS

| | | |
|---|---|---|
| EP | 0780124 | 6/1997 |
| FR | 2982486 | 5/2013 |
| JP | 5839651 | 3/1983 |
| JP | S58168697 | 10/1983 |
| WO | 9901126 | 1/1999 |
| WO | 2011022786 | 3/2011 |
| WO | 2011022786 A1 | 3/2011 |
| WO | 2015142999 A1 | 9/2015 |
| WO | 2017104277 | 6/2017 |
| WO | 2017104277 A1 | 6/2017 |
| WO | 2019026067 A1 | 2/2019 |

OTHER PUBLICATIONS

Freitag et al. Physiologia Plantarum 2012, 146: 160-172 (Year: 2012).*
Banskota A. H et al; "New diacylglyceryltrimethylhomoserines from the marine microalga Nannochloropsis granulata and their nitric oxide inhibitory activity"; Journal of Applied Phycology; vol. 25, No. 5, pp. 1513-1521, Jan. 8, 2013.
Khattib Ali et al; "Lyso-diacylglyceryltrimethylhomoserine (lyso-DGTS) isolated from Nannochloropsis microalgae improves high-density lipoprotein (HDL) functions" Bio Factors. vol. 46. No. 1, pp. 146-157, Oct. 29, 2019.
Ji Yeon Choi et al; "Inhibitory effect of ethanol extract of Nannochloropsis oceanica on lipopolysaccharide-inducei neuroinflammation, oxidative stress, amyloidogenesis and memory impairment" Oncotarget, vol. 8, No. 28, p. No. 45517-45530, Jul. 11, 2017.
Atrahimovich, D.; Vaya, J.; Khatib, S., "The effects and mechanism of flavonoid-rePON1 interactions. Structure-activity relationship study", Bioorganic & Medicinal Chemistry 2013, 21, 3348-3355.
Atrahimovich, D.; Vaya, J.; Tavori, H.; Khatib, S., "Glabridin Protects Paraoxonase 1 from Linoleic Acid Hydroperoxide Inhibition via Specific Interaction: a Fluorescence-Quenching Study", Journal of Agricultural and Food Chemistry 2012, 60, 3679-3685.
Barter, P. J.; Puranik, R.; Rye, K. A., "New Insights Into the Role of HDL as an Anti-inflammatory Agent in the Prevention of Cardiovascular Disease", Current cardiology reports 2007, 9, 493-498.
Ben-David, M.; Elias, M.; Filippi, J. J.; Dunach, E.; Silman, I.; Sussman, J. L.; Tawfik, D. S., "Catalytic Versatility and Backups in Enzyme Active Sites: The Case of Serum Paraoxonase 1", Journal of Molecular Biology 2012, 418, 181-196.
Cohen, E.; Aviram, M.; Khatib, S.; Artoul, F.; Rabin, A.; Mannheim, D.; Karmeli, R.; Salamon, T.; Vaya, J., "Human carotid plaque phosphatidylcholine specifically interacts with paraoxonase 1, increases its activity, and enhances its uptake by macrophage at the expense of its binding to HDL", Free radical biology & medicine 2014, 76, 14-24.

(Continued)

*Primary Examiner* — Matthew P Coughlin
(74) *Attorney, Agent, or Firm* — The Roy Gross Law Firm, LLC; Roy Gross

(57) ABSTRACT

The present invention relates to lyso-diacylglyceryltrimethylhomoserine (lyso-DGTS) or derivatives thereof for use in the treatment of atherosclerotic cardiovascular disease, and further provides particular such lyso-DGTS derivatives.

7 Claims, 10 Drawing Sheets

(56) References Cited

OTHER PUBLICATIONS

Craciun, E. C.; Leucuta, D. C.; Rusu, R. L.; David, B. A.; Cret, V.; Dronca, E., "Paraoxonase-1 activities in children and adolescents with type 1 diabetes mellitus", Acta Biochimica Polonica 2016, 63, 511-515.

Efrat, M.; Aviram, M., "Macrophage paraoxonase 1 (PON1) binding sites", Biochemical and Biophysical Research Communications 2008, 376, 105-110.

Fuhrman, B.; Volkova, N.; Aviram, M., "Postprandial serum triacylglycerols and oxidative stress in mice after consumption of fish oil, soy oil or olive oil: Possible role for paraoxonase-1 triacylglycerol lipase-like activity", Nutrition 2006, 22, 922-930.

Gu, X.; Huang, Y.; Levison, B. S.; Gerstenecker, G.; DiDonato, A. J.; Hazen, L. B.; Lee, J.; Gogonea, V.; DiDonato, J. A.; Hazen, S. L., "Identification of Critical Paraoxonase 1 Residues Involved in High Density Lipoprotein Interaction", The Journal of Biological Chemistry 2016, 291, 1890-1904.

Gugliucci, A.; Caccavello, R.; Nassar, H.; Abu Ahmad, W.; Sinnreich, R.; Kark, J. D., "Low protective PON1 lactonase activity in an Arab population with high rates of coronary heart disease and diabetes", Clinica chimica acta; International Journal of Clinical Chemistry 2015, 445, 41-47.

Gupta, N.; Binukumar, B. K.; Singh, S.; Sunkaria, A.; Kandimalla, R.; Bhansali, A.; Gill, K. D., "Serum paraoxonase-1 (PON1) activities (PONase/AREase) and polymorphisms in patients with type 2 diabetes mellitus in a North-West Indian population", Gene 2011, 487, 88-95.

Gur, M.; Cayli, M.; Ucar, H.; Elbasan, Z.; Sahin, D. Y.; Gozukara, M. Y.; Selek, S.; Koyunsever, N. Y.; Seker, T.; Turkoglu, C.; Kaypakli, O.; Aksoy, N., "Paraoxonase (PON1) activity in patients with subclinical thoracic aortic atherosclerosis", The International Journal of Cardiovascular Imaging 2014, 30, 889-895.

Hafiane, A.; Genest, J., "High density lipoproteins: Measurement techniques and potential biomarkers of cardiovascular risk", BBA clinical 2015, 3, 175-188.

Hatzihidiroglou, A.; Makedou, K.; Savopoulos, C., "Prevalence of paraoxonase-1 polymorphisms in diabetes mellitus type 2 Greek patients", Hippokratia 2016, 20, 176.

Hernaez, A.; Castaner, O.; Elosua, R.; Pinto, X.; Estruch, R.; Salas-Salvado, J.; Coralla, D.; Aras, F.; Serra-Majem, L.; Fiol, M.; Ortega-Calvo, M.; Ros, E.; Martinez-Gonzalez, M. A.; de la Torre, R.; Lopez-Sabater, M. C.; Fito, M., "Mediterranean Diet Improves High-Density Lipoprotein Function in High-Cardiovascular-Risk Individuals: A Randomized Controlled Trial", Circulation 2017, 135, 633-643.

Jamuna Rani, A.; Mythili, S. V.; Nagarajan, S., "Study on paraoxonase 1 in type 2 diabetes mellitus", Indian Journal of Physiology and Pharmacology 2014, 58, 13-16.

Jian, B.; de la Llera-Moya, M.; Ji, Y.; Wang, N.; Phillips, M. C.; Swaney, J. B.; Tall, A. R.; Rothblat, G. H., "Scavenger Receptor Class B type I as a Mediator of Cellular Cholesterol Efflux to Lipoproteins and Phospholipid Acceptors",The Journal of Biological Chemistry 1998, 273, 5599-5606.

Juretic, D.; Motejlkova, A.; Kunovic, B.; Rekic, B.; Flegar-Mestric, Z.; Vujic, L.; Mesic, R.; Lukac-Bajalo, J.; Simeon-Rudolf, V., "Paraoxonase/arylesterase in serum of patients with type II diabetes mellitus", Acta pharmaceutica 2006, 56, 59-68.

Khera, A. V.; Cuchel, M.; de la Llera-Moya, M.; Rodrigues, A.; Burke, M. F.; Jafri, K.; French, B. C.; Phillips, J. A. Mucksavage, M. L.; Wilensky, R. L.; Mohler, E. R.; Rothblat, G. H.; Rader, D. J., "Cholesterol Efflux Capacity, High-Density Lipoprotein Function, and Atherosclerosis", The New England Journal of Medicine 2011, 364, 127-135.

Levkau, B., "HDL-S1P: cardiovascular functions, disease-associated alterations, and therapeutic applications" Frontiers in Pharmacology 2015, 6, 243.

Lou-Bonafonte, J. M.; Gabas-Rivera, C.; Navarro, M. A.; Osada, J., "The Search for Dietary Supplements to Elevate or Activate Circulating Paraoxonases", International Journal of Molecular Sciences 2017, 18, 416.

Mackness, M.; Mackness, B., "Human paraoxonase-1 (PON1): Gene structure and expression, promiscuous activities and multiple physiological roles", Gene 2015, 567, 12-21.

Miller, N. E.; La Ville, A.; Crook, D., "Direct evidence that reverse cholesterol transport is mediated by high-density lipoprotein in rabbit", Nature 1985, 314, 109-111.

Noack, B.; Aslanhan, Z.; Boue, J.; Petig, C.; Teige, M.; Schaper, F.; Hoffmann, T.; Hannig, C., "Potential Association of Paraoxonase-1, Type 2 Diabetes Mellitus, and Periodontitis", Journal of Periodontology 2013, 84, 614-623.

Nofer, J. R.; Assmann, G., "Atheroprotective Effects of High-Density Lipoprotein-Associated Lysosphingolipids", Trends in Cardiovascular Medicine 2005, 15, 265-271.

Dram, J., "HDL Apolipoprotein and ABCA1. Partners in the removal of excess cellular cholesterol", Arteriosclerosis, thrombosis, and vascular biology 2003, 23, 720-727.

Pirillo, A.; Norata, G. D.; Catapano, A. L., "Treating High Density Lipoprotein Cholesterol (HDL-C): Quantity Versus Quality", Current Pharmaceutical design 2013, 19, 3841-3857.

Poti, F.; Simoni, M.; Nofer, J. R., "Atheroprotective role of high-density lipoprotein (HDL)-associated sphingosine-1-phosphate (S1P)", Cardiovascular Research 2014, 103, 395-404.

Rosenblat, M.; Gaidukov, L.; Khersonsky, O.; Vaya, J.; Oren, R.; Tawfik, D. S.; Aviram, M., "The Catalytic Histidine Dyad of High Density Lipoprotein-associated Serum Paraoxonase-1 (PON1) Is Essential for PON1-mediated Inhibition of Low Density Lipoprotein Oxidation and Stimulation of Macrophage Cholesterol Efflux", The Journal of Biological Chemistry 2006, 281, 7657-7665.

Rosenblat, M.; Vaya, J.; Shih, D.; Aviram, M., "Paraoxonase 1 (PON1) enhances HDL-mediated macrophage cholesterol efflux via the ABCA1 transporter in association with increased HDL binding to the cells: a possible role for lysophosphatidylcholine", Atherosclerosis 2005, 179, 69-77.

Rozenberg, O.; Rosenblat, M.; Coleman, R.; Shih, D. M.; Aviram, M., "Paraoxonase (PON1) Deficiency is Associated with Increased Macrophage Oxidative Stress: Studies in PON1-Knockout Mice", Free Radical Biology & Medicine 2003, 34, 774-784.

Rozenberg, O.; Shih, D. M.; Aviram, M., "Human Serum Paraoxonase 1 Decreases Macrophage Cholesterol Biosynthesis: Possible Role for Its Phospholipase-A2-Like Activity and Lysophosphatidylcholine Formation", Arteriosclerosis, Thrombosis, and Vascular Biology 2003, 23, 461-467.

Santos-Gallego, C. G., "HDL: Quality or quantity?" Atherosclerosis 2015, 243, 121-123.

Sattler, K.; Graler, M.; Keul, P.; Weske, S.; Reimann, C. M.; Jindrova, H.; Kleinbongard, P.; Sabbadini, R.; Brocker-Preuss, M.; Erbel, R.; Heusch, G.; Levkau, B., "Defects of High-Density Lipoproteins in Coronary Artery Disease Caused by Low Sphingosine-1-Phosphate Content: Correction by Sphingosine-1-Phosphate-Loading", Journal of the American College of Cardiology 2015, 66, 1470-1485.

Sattler, K.; Levkau, B., "Sphingosine-1-phosphate as a mediator of high-density lipoprotein effects in cardiovascular protection", Cardiovascular Research 2009, 82, 201-11.

Shih, D. M.; Welch, C.; Lusis, A. J., "New insights into atherosclerosis from studies with mouse models", Molecular Medicine Today 1995, 1, 364-372.

Shih, D. M.; Xia, Y. R.; Wang, X. P.; Miller, E.; Castellani, L. W.; Subbanagounder, G.; Cheroutre, H.; Faull, K. F.; Berliner, J. A.; Witztum, J. L.; Lusis, A. J., "Combined Serum Paraoxonase Knockout/Apolipoprotein E Knockout Mice Exhibit Increased Lipoprotein Oxidation and Atherosclerosis", The Journal of Biological Chemistry 2000, 275, 17527-17535.

Sun, Y.; Zhang, H.; Sun, Y.; Zhang, Y.; Liu, H.; Cheng, J.; Bi, S.; H., Z., "Study of interaction between protein and main active components in Citrus aurantium; L. by optical spectroscopy", Journal of Luminescence 2010, 130, 270-279.

Fang, W. H.; Hartiala, J.; Fan, Y.; Wu, Y.; Stewart, A. F.; Erdmann, J.; Kathiresan, S.; Consortium, C. A.; Roberts, R.; McPherson, R.;

(56) References Cited

OTHER PUBLICATIONS

Allayee, H.; Hazen, S. L., "Clinical and Genetic Association of Serum Paraoxonase and Arylesterase Activities with Cardiovascular Risk", Arteriosclerosis, Thrombosis, and Vascular Biology 2012, 32, 2803-2812.

Tavori, H.; Aviram, M.; Khatib, S.; Musa, R.; Mannheim, D.; Karmeli, R.; Vaya, J., "Human carotid lesion linoleic acid hydroperoxide inhibits paraoxonase 1 (PON1) activity via reaction with PON1 free sulfhydryl cysteine 284", Free Radical Biology & Medicine 2011a, 50, 148-156.

Tavori, H.; Aviram, M.; Khatib, S.; Musa, R.; Mannheim, D.; Karmeli, R., Vaya, J., "Paraoxonase 1 protects macrophages from atherogenicity of a specific triglyceride isolated from human carotid lesion", Free Radical Biology & Medicine 2011b, 51, 234-242.

Tavori, H.; Aviram, M.; Khatib, S.; Musa, R.; Nitecki, S.; Hoffman, A.; Vaya, J., "Human carotid atherosclerotic plaque increases oxidative state of macrophages and low-density lipoproteins, whereas paraoxonase 1 (PON1) decreases such atherogenic effects", Free Radical Biology & Medicine 2009, 46, 607-615.

Tavori, H.; Khatib, S.; Aviram, M.; Vaya, J., "Characterization of the PON1 active site using modeling simulation, in relation to PON1 lactonase activity", Bioorganic & Medicinal Chemistry 2008, 16, 7504-7509.

Yuhanna, I. S.; Zhu, Y.; Cox, B. E.; Hahner, L. D.; Osbome-Lawrence, S.; Lu, P.; Marcel, Y. L.; Anderson, R. G.; Mendelsohn, M. E.; Hobbs, H. H.; Shaul, P. W., "High-density lipoprotein binding to scavenger receptor-BI activates endothelial nitric oxide synthase", Nature medicine 2001, 7, 853-857.

Zakiev, E.; Feng, M.; Sukhorukov, V.; Kontush, A., "HDL-Targeting Therapeutics: Past, Present and Future", Current Pharmaceutical Design 2017, 23, 1207-1215.

Zheng, C.; Aikawa, M., "High-density Lipoproteins: From Function to Therapy", Journal of the American College of Cardiology 2012, 60, 2380-2383.

Chaofu Ke et al; "Large-scale profiling of metabolic dysregulation in ovarian cancer"; International Journal of Cancer; vol. 136, pp. 516-526, 2015.

Jee S.H. et al.; "Clinical relevance of glycerophospholipid, sphingomyelin and glutathione metabolism in the pathogenesis of pharyngolaryngeal cancer in smokers: the Korean Cancer Prevention Study-II"; Metabolomics; vol. 12, No. 164, 2016.

Ohsumi T. et al.; "N.EPSILON.-Acyllysine Derivatives Inhibit Aspartokinase in Brevibacterium lactofermentum" Bioscience Biotechnology and Biochemistry; vol. 58, No. 7, pp. 1351-1352, Jan. 1994.

Bell F.P; "Carnitine Ester Hydrolysis in Arteries From Normal and Cholesterol-Fed Rabbits and the Effects of Carnitine Esters on Arterial Microsomal ACAT"; Comp Biochem Physiol B; vol. 79, No. 2, pp. 125-128, 1984.

Deguchi H. et al.; "Acylcarnitines are Anticoagulants that inhibit factor Xa and are reduced in Venous Thrombosis, based on Metabolomics Data"; Blood; vol. 126, No. 13, pp. 1595-1600, Sep. 24, 2015.

Back M. et al.; "Anti-inflammatory therapies for Atherosclerosis"; Nature Reviews Cardiology; vol. 12, No. 4, pp. 199-211, Apr. 2015.

Charo I. F et al.; "Anti-inflammatory therapeutics for the treatment of Atherosclerosis"; Nature Reviews Drug Discovery, vol. 10, No. 5, pp. 365-376, May 2011.

Dahli L. et al.; "Lyso-DGTS Lipid isolated from Microalgae Enhances PON1 Activities in Vitro and in Vivo, increases PON1 Penetration into Macrophages and decreases Cellular Lipid Accumulation"; Biofactors; vol. 44, No. 3, pp. 299-310, May 2018.

Khatib S. et al.; "*Nannochloropsis* sp. ethanol extract prevents macrophage and LDL oxidation and enhances PON1 activity through the principal active compound lyso-diacylglyceryltrimethylhomoserine (lyso-DGTS)"; Journal of Applied Phycology; vol. 30, pp. 1679-1689, 2018.

Yoon J. Y et al.; "A direct protein kinase B-targeted anti-inflammatory activity of cordycepin from artificially cultured fruit body of Cordyceps militaris"; Pharmacognosy Magazine.; vol. 11, No. 43, pp. 477-485, Jul.-Sep. 2015.

International Search Report, International Application No. PCT/IL2018/050924, dated Dec. 11, 2018.

Mackness, et al., "Low Paraoxonase Activity Predicts Coronary Events in the Caerphilly Prospective Study", Circulation vol. 107 (2003).

Chaofu Ke et al: "Large-scale profiling of metabolic dysregulation in ovarian cancer", Int. J. Cancer: 136, 516-526 (2015) VC 2014 UICC.

Sun Ha Jee: "Clinical relevance of glycerophospholipid, sphingomyelin and glutathione metabolism in the pathogenesis of pharyngolaryngeal cancer in smokers: the Korean Cancer Prevention Study-II", Metabolomics (2016) 12:164 DOI 10.1007/s11306-016-1114-6.

Tsuyoshi Ohsumi: "Nε-Acyllysine Derivatives Inhibit Aspartokinase in Brevibacterium lactofermentum", Bioscience, Biotechnology, and Biochemistry, 58:7, 1351-1352, DOI: 10.1271/bbb.58.1351 (1994).

\* cited by examiner

COMPOSITIONS AND METHODS FOR TREATING ATHEROSCLEROTIC CARDIOVASCULAR DISEASE

CROSS-REFERENCE TO RELATED APPLICATIONS

This application is a National Phase of PCT Patent Application No. PCT/IL2018/050924 having International filing date of Aug. 22, 2018, which claims the benefit of priority of U.S. Provisional Patent Application No. 62/549,058, filed on Aug. 23, 2017 and U.S. Provisional Patent Application No. 62/621,261, filed on Jan. 24, 2018. The contents of the above applications are all incorporated by reference as if fully set forth herein in their entirety

TECHNICAL FIELD

The present invention provides pharmaceutical compositions and methods for treatment of atherosclerotic cardiovascular disease.

BACKGROUND ART

Atherosclerosis is a multifactorial disease and the usual cause of heart attacks, strokes, and peripheral vascular disease, together referred to as "cardiovascular disease" (CVD). Atherosclerotic CVD is a pathological process characterized by the deposition of lipids and compounds within the arterial wall, and is considered the major cause of morbidity and mortality in the western world.

Lowering of low density lipoprotein (LDL)-cholesterol using 3-hydroxy-3-methylglutaryl coenzyme A reductase inhibitors (statins) has become an integral component of strategies to reduce cardiovascular risk; however, statins reduce CVD risk by no more than 40%, and they have some side effects such as muscle pain and damage, liver problems, digestive problems, rash or flushing, blood glucose elevation, and memory loss or confusion. Modulation of high density lipoprotein (HDL) become to be an alternative strategy for reducing CVD risk due to its antiatherogenic properties such as reverse cholesterol transport (Khera et al., 2011; Miller et al., 1985), antioxidant, anti-inflammatory (Barter et al., 2007), anti-apoptotic, vasodilatory and cytoprotective effects, and endothelial function improvement (Nofer et al., 2005; Yuhanna et al., 2001). In the last several years, there is growing evidence from epidemiological data, animal studies, and clinical trials supporting HDL as the next target to reduce residual cardiovascular risk in statin-treated, high-risk patients (Zakiev et al., 2017). However, the hypothesis that raising HDL-cholesterol (HDL-C) levels will result in reduction of CVD risk has never been really confirmed. Methods developed to increase blood HDL levels failed to reduce CVD risk. For example, clinical trials using cholesteryl ester transfer protein inhibitors were terminated due to excess adverse events and futility despite a 72% increase in blood HDL cholesterol levels. Nicotinic acid and fabric acid derivatives increased HDL cholesterol levels, but linking these increases to clinical risk reduction has been questionable. Instead, recent studies indicate that the focus should be on improving HDL functions (HDL "quality"), which truly reflect and are responsible for the actual beneficial effects of HDL, rather than increasing HDL-C levels (HDL-C "quantity") (Santos-Gallego et al., 2015; Zheng et al., 2012; Pirillo et al., 2013).

HDL comprises a heterogeneous family of lipoprotein species, differing in surface charge, size, and lipid and protein compositions (Hafiane et al., 2015). A lipid such as sphingosine-1-phosphate (S1P) has been recently discovered to be both a mechanistic cause and a therapeutic target for HDL dysfunction (Sattler et al., 2009). Coronary artery disease (CAD) patients exhibited lower HDL-bound S1P than healthy volunteers, while CAD-HDL was found dysfunctional, demonstrating lower endothelial signaling activation and vasodilatation induction. Supplementation of SIP to animals with HDL dysfunction reversed HDL quality (Levkau et al., 2015; Poti et al., 2014; Sattler et al., 2015).

Most of the HDL functional and atheroprotective effects are also attributed to its associated enzyme paraoxonase 1 (PON1; EC 3.1.8.1) (Gu et al., 2016). PON1-deficient mice were found susceptible to the development of atherosclerosis, while overexpression of human PON1 in mice inhibits its development (Shih et al., 1995; 2000). PON1 activity has been inversely correlated with carotid intima-media thickness (Gur et al., 2014), attenuates oxidized-LDL uptake by macrophage, inhibits macrophage cholesterol biosynthesis rate, and stimulates HDL-mediated cholesterol efflux from macrophage (Cohen et al., 2014; Tavori et al., 2009, 2011a, 2011b). Epidemiological evidence demonstrates that low PON1 activity is associated with increased risk of cardiovascular events and CVD (Gugliucci et al., 2015). PON1 has many activities towards organophosphate triesters, arylesters, cyclic carbamates, glucuronides, oestrogen esters and thiolactones, whereas the "natural" substrates of PON1 assume to be lactones (Tavori et al., 2008). As an antioxidant enzyme carried by HDL, PON1 can hydrolyze lipid peroxide in lipoproteins through its lipolactonase activity which, thus decreases oxidative stress in serum lipoproteins, macrophages, and atherosclerotic lesions (Rosenblat et al., 2006; Ben-David et al., 2012).

Microalgae are used as food source and as addible feed in aquaculture for production of mollusks and some fish species. Microalgae have been recognized as potentially good sources for biofuel production because of their high oil content and rapid biomass production. Components of algae are frequently used in cosmetics as thickening agents, water-binding agents, and antioxidants. Microalgae extracts are widely used as therapeutic and food supplements due to their high content of carotenoids, phenolic compounds including polyphenols, and lipids such as phospholipids, whole and unhydrolyzed glycolipids, lysolipids, free fatty acids, waxes, and sterols and sterols esters.

Several microalgae, including *Nannochloropsis* sp. and *Nannochloropsis salina*, have been described as potential sources of omega-3 fatty acids such as eicosapentaenoic acid (EPA) and docosahexaenoic acid (DHA).

SUMMARY OF INVENTION

In one aspect, the present invention provides a pharmaceutical composition for treatment of atherosclerotic cardiovascular disease, comprising a pharmaceutically acceptable carrier and a compound of the formula I:

$$R_1-C(O)-R_2-R_3-COOH \quad\quad I$$

wherein
$R_1$ is $(C_{15}-C_{21})$alkyl, $(C_{15}-C_{21})$alkenyl, or $(C_{15}-C_{21})$alkynyl;
$R_2$ is —O—$CH_2$—$CHR_4$—$CH_2$—O—, —NH—$CH_2$—$CHR_4$—$CH_2$—O—, —O—, or —NH—;
$R_3$ is $(C_1-C_8)$alkylene substituted with a group of the formula —$N^+(R_5)_3$, and optionally further substituted with one or more —OH groups;
$R_4$ is —OH, —O—C(O)—$R_6$, or —NH—C(O)—$R_6$;
$R_5$ each independently is $(C_1-C_8)$alkyl; and $R_6$ is $(C_{15}-C_{21})$alkyl, $(C_{15}-C_{21})$alkenyl, or $(C_{15}-C_{21})$alkynyl, or a pharmaceutically acceptable salt or solvate thereof.

In another aspect, the present invention relates to a compound of the formula I as defined above, or a pharmaceutically acceptable salt or solvate thereof, for use in the treatment of atherosclerotic cardiovascular disease.

In yet another aspect, the present invention relates to use of a compound of the formula I as defined above, or a pharmaceutically acceptable salt or solvate thereof, for the preparation of a pharmaceutical medicament for treatment of atherosclerotic cardiovascular disease.

In still another aspect, the present invention relates to a method for treatment of atherosclerotic cardiovascular disease in a subject in need thereof, comprising administering to said subject a therapeutically effective amount of a compound of the formula I as defined above, or a pharmaceutically acceptable salt or solvate thereof.

In a further aspect, the present invention provides a compound of the formula I as defined above, but excluding the compounds wherein $R_2$ is —O—$CH_2$—$CHR_4$—$CH_2$—O—, i.e., a compound of the formula I wherein $R_2$ is —NH—$CH_2$—$CHR_4$—$CH_2$—O—, —O—, or —NH—.

In yet a further aspect, the present invention provides a pharmaceutical composition comprising a compound of the formula I as defined above but excluding the compounds wherein $R_2$ is —O—$CH_2$—$CHR_4$—$CH_2$—O—, or a pharmaceutically acceptable salt or solvate thereof, and a pharmaceutically acceptable carrier.

BRIEF DESCRIPTION OF DRAWINGS

FIG. 6A shows a histogram showing the shift of mean fluorescence intensity (MFI) of a representative experiment in cells incubated with rePON1 without FITC (negative control), cells incubated with FITC-rePON1; and cells incubated with FITC-rePON incubated with lyso-DGTS at 10, 20, 50, and 100 μg/ml. The average of the MFI is shown in FIG. 6B. ***$p<0.0001$ related to the control (cells incubated with FITC-rePON1 alone; n=3). Statistic was analyzed using one-way ANOVA Graphpad prism 5 software (FL1-H-relative FITC fluorescence intensity (height) in the FL1 channel).

DETAILED DESCRIPTION

Figure 1A:
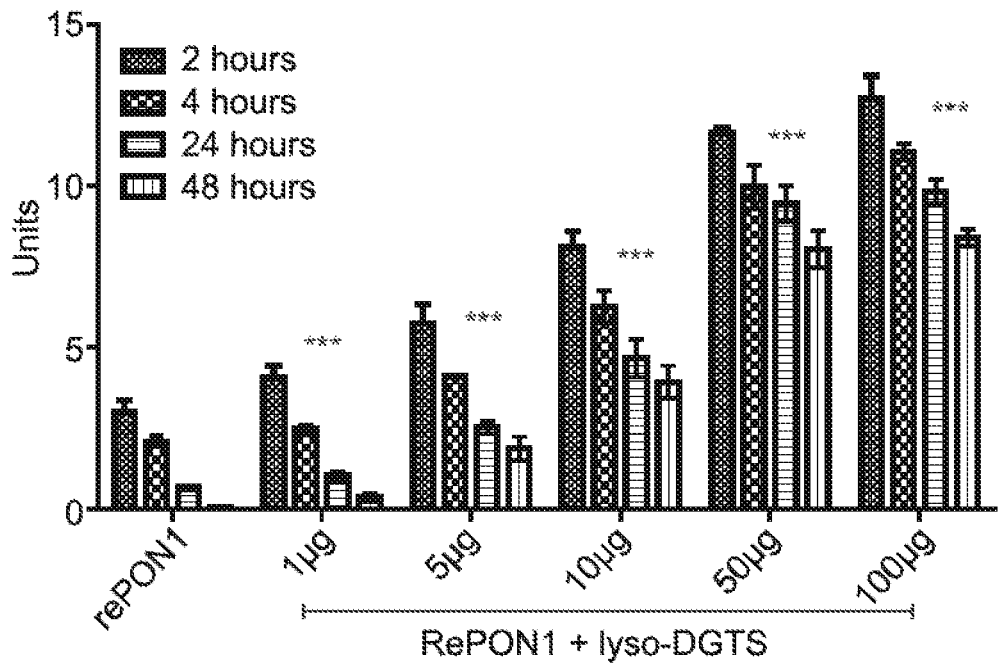
FIGS. 1A-1B show lactonase activity of rePON1 after incubation with lyso-DGTS at concentrations of 0, 1, 5, 10, 50, and 100 μg/ml for 2, 4, 24, or 48 h at 37° C. in Tris buffer pH=8.4 (1A); and arylesterase activity of rePON1 after incubation with lyso-DGTS at concentrations of 0, 1, 5, 10, 50, and 100 μg/ml for 2 or 4 h at 37° C. in Tris buffer pH=8.4 (1B). Each experiment was repeated separately at least three times. *$p<0.05$, ***$p<0.0001$ related to the control (rePON1 without lyso-DGTS). Statistics were analyzed using one-way ANOVA and Graphpad prism 5 software.

As found in accordance with the present invention, extracts of the microalgae *Nannochloropsis salina* and *Nannochloropsis oculata* contain an active substance that protects PON1 from oxidation and increases its lactonase and arylesterase activities, and inhibits LDL and macrophage oxidation. As particularly found, an ethanol water (70:30%) extract of the microalgae *Nannochloropsis salina* and *Nannochloropsis oculata* increased recombinant PON1 (re-PON1) activities in a dose-dependent manner, and stabilized and preserved rePON1 activity for at least 48 hours.

Analysis of said ethanol water extract using LC-MS and NMR methods has revealed that the active substance comprised within said extract is lyso-diacylglyceryltrimethylhornmoserine (lyso-DGTS, herein identified compound Ia-12, when n is 2; and $R_5$ is methyl), a betaine lipid derivative, abundant in the membranes of many algae, lower plants and fungi, and composed of EPA (C20:5) fatty acid connected to glyceryl-trimethyl-homoserine (C20:5 lyso-DGTS lipid). This compound resembles S1P structure, as both contain a hydrophobic element (the C:15:1(Δ2) in the sphingosine and EPA in the lyso-DGTS), and a polar element in the other side of the molecule (phosphoric acid vs. trimethyl homoserine).

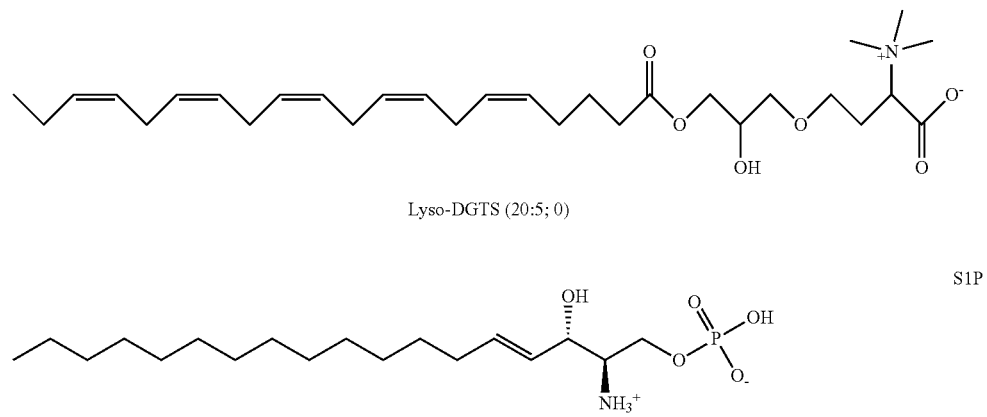

As stated above, the beneficial effects of HDL have been partly attributed to its antioxidant properties mediated by PON1. According to the literature, the hydrolytic lactonase, arylesterase, and paraoxonase activities of PON1 are all inactivated under oxidative stress, and epidemiological evidences demonstrate that low serum PON1 lactonase activity is associated with increased risk of coronary heart disease and diabetes (Mackness et al., 2003 and 2015; Fuhrman et al., 2006). Moreover, lower serum arylesterase provided incremental prognostic value and clinical reclassification of stable subjects at risk of cardiovascular events (Tang et al., 2012).

Based on the above, pharmacological and nutritional modulation of PON1 activity and/or gene expression could constitute a useful approach for improving HDL functions and prevention of cardiovascular diseases (Hernaez et al., 2017; Lou-Bonafonte et al., 2017). As previously shown, various endogenous and exogenous molecules, e.g., nutrients, can non-covalently interact with PON1 and affect its properties (increase or decrease its activity/stability, prevent its free thiol oxidation, affect its influx into cells, and affect cytosolic triglyceride accumulation). Lipids such as phosphatidylcholines interact with PON1 and increase its activity (Atrahimovich et al., 2012; Cohen et al., 2014).

As shown herein, lyso-DGTS increases rePON1 lactonase and arylesterase activities in a dose and time dependent manner, and stabilizes and preserves rePON1 lactonase activity for at least 48 hours. Moreover, increase in the PON1 lactonase activity in a dose dependent manner was also observed following incubation of lyso-DGTS with the whole human serum.

Protein activities can be affected and may be altered by their interaction with small molecules in their milieu. In order to understand the mechanism by which lyso-DGTS affects PON1 activities, a tryptophan (Trp) fluorescence quenching assay was carried out to indicate possible interaction between lyso-DGTS and rePON1. PON1 contains four Trp amino acid residues and the Trp fluorescence quenching assay measures the affinity of the interaction between the protein and lyso-DGTS that results in changes in PON1 3D structure, and consequently in alteration in the protein Trp fluorescence. As shown herein, increasing lyso-DGTS concentrations decreased the intensity of rePON1 fluorescence in a dose dependent manner at both 25° C. and 37° C.

Stern-Volmer plot did not show any deviation from linearity toward the y axis at the reported lyso-DGTS concentrations, and the Ksv values obtained indicated a static quenching process initiated by lyso-DGTS, suggesting a specific interaction between rePON1 and lyso-DGTS. Binding constant (Ka) and thermodynamic parameters calculations revealed decrease in binding constant with increasing temperature (the best association appeared to be at 298° K). The values obtained for the number of binding sites per rePON1 (n) were not affected by the temperature and were found to be ~1, indicating the existence of a single binding site for lyso-DGTS in rePON1. Thermodynamic parameters were calculated to elucidate the lyso-DGTS-PON1 interaction. A negative $\Delta G$ was observed, indicating that the interaction is spontaneous, and negative values for both $\Delta H$ and $\Delta S$ indicated that the dominating force is a van der Waals or/and hydrogen bond (Sun et al., 2010).

In accordance with the fluorescence analysis, docking analysis has shown that lyso-DGTS binds to PON1 with a negative binding energy, indicating a spontaneous interaction dominated by van der Waals and hydrogen bonds forces.

The interaction site of phosphatidylcholines (PCs) with PON1, obtained from the molecular docking analysis, was near the α-helix H2, which together with α-helix H1 forms a hydrophobic patch that binds the protein to the HDL surface. This interaction interrupts the ability of PON1 to bind to the HDL particle at the expense to its binding to PC. PC 16:0 18:2, demonstrated the highest affinity to PON1 relative to other PCs examined, and decreased the ratio between HDL-PON1 and free-PON1 by 50%. The interaction affinity of rePON1 with lyso-DGTS was found to be higher in one-fold order than that of PC 16:0 18:2 (Cohen et al., 2014). The Ka of lyso-DGTS at 25° C. and 37° C. was $1.052 \times 10^4$ (M$^{-1}$) and $2.377 \times 10$ (M$^{-1}$), respectively, while the Ka for PC 16:0 18:2 was $1.68 \times 10^3$ (M$^{-1}$) at 25° C. As shown herein, lyso-DGTS interacts with PON1 in a different site than PC 16:0 18:2, far from H1 and H2, and therefore in contrast to PC, does not affect PON1 binding to HDL. The ratio between HDLbound-PON1 vs. free-PON1 did not change (data not shown).

As previously shown, PON1 specifically internalized into the cytoplasm of macrophage cells through endocytosis and may thus protect these cells from oxidation and prevent foam cell formation. As further shown, phosphatidylcholine lipids, and particularly PC 16:0 18:2, enhance PON1 uptake by macrophage cells. As shown herein, lyso-DGTS lipid significantly increases rePON1 internalization into macrophage cells in a dose dependent manner, which can be a useful mechanism for macrophage defense, considering that PON1 protects macrophage cells from oxidative stress (Rozanberg et al., 2003) and from plaque triglyceride damage (Tavori et al., 201 b; 2009), and decreases macrophage cholesterol biosynthesis (Rozanberg et al., 2003).

Macrophage cells uptake of ox-LDL forming foam cell is the hallmark for atherosclerosis. Macrophage cells via their scavenger receptors take up ox-LDL and other lipids, undergo activation, produce cytokines and reactive oxygen species (ROS), and differentiate into foam cells to form the early lesions stage. Incubation of macrophage cells with ox-LDL resulted in lipid deposition in the cells and foam cell formation. The quantitative analysis of oil red staining intensity showed that pre-incubation of cells with lyso-DGTS alone significantly reduced oil red staining intensity. Pre-incubation of the cells with rePON1 or rePON1 incubated with lyso-DGTS also significantly decreased oil red staining intensity, confirming that lyso-DGTS alone, and lyso-DGTS incubated with rePON1, can inhibit ox-LDL-induced foam cell formation.

HDL removes cholesterol from cells including macrophage cells, and this is considered to represent a major atheroprotective function of HDL particles. A link between the in vitro efflux of cholesterol from macrophage cells and atherosclerosis has recently been established by studies demonstrating a negative correlation between cholesterol efflux from J774 mouse cells and coronary artery disease. HDL removes excess cholesterol from arterial cells, including macrophage foam cells, via the scavenger receptor B1 (SR-BI) and the ATP binding cassette transporter A1 (ABCA1) (Jian et al., 1998; Oram et al., 2003). Previous studies have shown that PON1 enhances HDL-mediated macrophage cholesterol efflux via the ABCA1 transporter in association with increased HDL binding to the cells (Rosenblat et al., 2005). As demonstrated herein, lyso-DGTS enhanced HDL-mediated macrophage cholesterol efflux, and significantly increased the ability of HDL to take out cholesterol from macrophages in a dose dependent manner.

The effect of lyso-DGTS on PON1 activity and clinical parameters was examined using in vivo experiments. Balb/c mice were fed with a high fat diet (HFD) for 12 weeks, and during the last 4 weeks they were supplemented with lyso-DGTS. The administration of lyso-DGTS to the circulation was carried via subcutaneously implanted osmotic mini-pumps. This technique ensures continuous exposure of the tested compound at a desired concentrations and period. At the end of the treatment period, the mice were sacrificed, and clinical parameters were analyzed. Serum lactonase PON1 activity was significantly decreased in mice fed with high fat diet while administration of lyso-DGTS significantly increased serum lactonase activity to the level of the control (mice fed with normal diet). Studies with different ethnic groups have shown that lower PON1 activities are associated with type 2 and type 1 diabetes (Hatzihidiroglou et al., 2016; Jamuna Rani et al., 2014; Noack et al., 2013; Gupta et al., 2011; Juretic et al., 2006; Cracium et al., 2016). A non-significant increase in serum glucose concentrations was observed in the mice group treated with HFD compared to the non-treated group, whereas their lactonase PON1 activity decreased significantly. Interestingly, the group treated with lyso-DGTS showed decrease in serum glucose concentrations in parallel to increase of serum lactonase activity (both statistically significant), demonstrating values similar to those shown by the non-treated group (mice fed with normal diet). These findings demonstrate a correlation between PON1 lactonase activity and serum glucose levels.

In conclusion, the studies described herein demonstrate that lyso-DGTS interacts with rePON1 and increases its lactonase and aryl esterase activity in a dose dependent manner; increases human serum PON1 lactonase activity in a dose dependent manner; enhances rePON1 influx into macrophage cells in a dose dependent manner; decreases the deposition of lipids induced by ox-LDL; and increases HDL mediated cholesterol efflux, and may thus protect macrophage cells from oxidation and prevent foam formation. In addition, serum taken from mice fed with HFD and treated with lyso-DGTS shows increased lactonase PON1 activity and decreased glucose concentration that is, in fact, similar to that of mice fed with regular diet. These findings suggest that lyso-DGTS has a potential to decrease atherosclerosis risk by enhancing PON1 activity, improving HDL quality, protecting macrophages, and preventing foam cells formation, and may thus decrease CVD.

In one aspect, the present invention thus provides a pharmaceutical composition for treatment of atherosclerotic cardiovascular disease, comprising a pharmaceutically acceptable carrier and a compound of the formula I as defined above, herein referred to as the "active agent".

The compound of the formula I may have one of the four sub-structures referred to herein as formulas Ia, Ib, Ic and Id, and shown in Table 1. A compound of the formula Ia consists of a saturated or unsaturated fatty acid residue linked via ester bond to one of the terminal carbon atoms of glyceryl (—O—CH$_2$—CHR$_4$—CH$_2$O—), wherein the other terminal carbon atom of the glyceryl is linked via ether bond to a terminal carbon atom of the side chain of an alpha amino acid having a quaternary ammonium. The compound of the formula Ib has a structure similar to that of Ia, wherein the glyceryl nuclei is replaced with a ceramide-like nuclei having an amino group on one of the terminal carbon atoms (—NH—CH$_2$—CHR$_4$—CH$_2$O—). Such a compound thus consists of a saturated or unsaturated fatty acid residue linked via amide bond to the terminal carbon atom of the ceramide-like nuclei, wherein the other terminal carbon atom of the ceramide-like nuclei is linked via ether bond to a terminal carbon atom of the side chain of an alpha amino acid having a quaternary ammonium. The compound of the formula Ic has neither glyceryl nor ceramide-like nuclei, and it consists of a saturated or unsaturated fatty acid residue linked directly, via ester bond, to a terminal carbon atom of the side chain of an alpha amino acid having a quaternary ammonium. The compound of the formula Id has a structure similar to that of Ic, wherein the ester bond is replaced with an amide bond, and it thus consists of a saturated or unsaturated fatty acid residue linked directly, via amide bond, to a terminal carbon atom of the side chain of an alpha amino acid having a quaternary ammonium. Specific compounds of the formulas Ia, Ib, Ic and Id described herein are herein identified compounds Ia-1 to Ia-14, Ib-1 to Ib-14, Ic-1 to Ic-14, and Id-1 to Id-14, and are shown in Tables 2-3.

TABLE 1

General structures of formulas Ia, Ib, Ic and Id

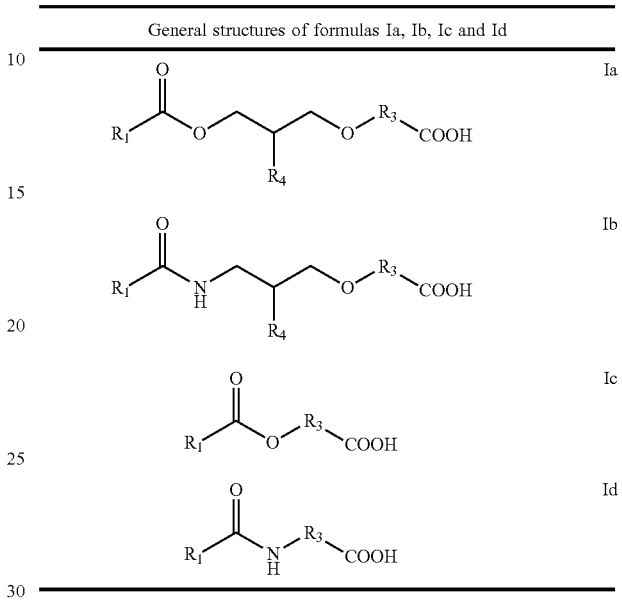

*R$_1$, R$_3$ and R$_4$ are each as defined above.

The term "alkyl" as used herein typically means a linear or branched saturated hydrocarbon radical. The term (C$_1$-C$_8$)alkyl denotes such a radical having 1-8 carbon atoms and includes, e.g., methyl, ethyl, n-propyl, isopropyl, n-butyl, sec-butyl, isobutyl, tert-butyl, 2-methylpropyl, n-pentyl, isopentyl, neopentyl, 2-methylbutyl, 1,1-dimethylpropyl, 2,2-dimethylpropyl, n-hexyl, isohexyl, 2-methylpentyl, 3-methylpentyl, 1,1-dimethylbutyl, 2,2-dimethylbutyl, 2-ethylbutyl, n-heptyl, 2-methylhexyl, 1,1-dimethylpentyl, 1,2-dimethylpentyl, 1,1,2-trimethylbutyl, n-octyl, 2-methylheptyl, 1,1-dimethylhexyl, 1,2-dimethylhexyl, 1,1,2-trimethylpentyl, and the like, wherein preferred are (C$_1$-C$_6$)alkyl or (C$_1$-C$_4$)alkyl groups such as methyl, ethyl, n-propyl, isopropyl, or n-butyl. The term "(C$_{15}$-C$_{21}$)alkyl" denotes such a radical having 15-21 carbon atoms, i.e., (C$_{15}$)alkyl, (C$_{16}$)alkyl, (C$_{17}$)alkyl, (C$_{18}$)alkyl, (C$_{19}$)alkyl, (C$_{20}$)alkyl, or (C$_{21}$)alkyl, wherein preferred are (C$_{15}$)alkyl, (C$_{17}$)alkyl, (C$_{19}$)alkyl, and (C$_{21}$)alkyl groups, more specifically linear (C$_{15}$)alkyl, (C$_{17}$)alkyl, (C$_{19}$)alkyl, and (C$_{21}$)alkyl groups.

The terms "alkenyl" and "alkynyl" typically mean linear or branched hydrocarbon radicals having at least one, e.g., one, two, three, four, five, or six, double bond or triple bond, respectively. The terms "(C$_{15}$-C$_{21}$)alkenyl" and "(C$_{15}$-C$_{21}$)alkynyl" denote such hydrocarbon radicals having 15-21 carbon atoms. Examples of such alkenyls include, without being limited to, (C$_{15}$)alkenyl, (C$_{16}$)alkenyl, (C$_{17}$)alkenyl, (C$_{18}$)alkenyl, (C$_{19}$)alkenyl, (C$_{20}$)alkenyl, or (C$_{21}$)alkenyl, having at least one double bond, wherein preferred are (C$_{17}$)alkenyl, (C$_{19}$)alkenyl, or (C$_{21}$)alkenyl. Examples of such alkynyls include, without limitation, (C$_{15}$)alkynyl, (C$_{16}$)alkynyl, (C$_{17}$)alkynyl, (C$_{18}$)alkynyl, (C$_{19}$)alkynyl, (C$_{20}$)alkynyl, or (C$_{21}$)alkynyl, having at least one triple bond.

The term "alkylene" typically means a divalent linear or branched hydrocarbon radical. The term "(C$_1$-C$_8$)alkylene"

denotes such a divalent hydrocarbon radical having 1-8 carbon atoms and includes, e.g., methylene, ethylene, propylene, butylene, 2-methylpropylene, pentylene, 2-methylbutylene, hexylene, 2-methylpentylene, 3-methylpentylene, 2,3-dimethylbutylene, heptylene, octylene, and the like. Preferred are $(C_1-C_6)$alkylenes or $(C_1-C_4)$alkylenes such as methylene, ethylene, propylene, or butylene.

The term "amino acid" as used herein refers to an organic compound comprising both quaternary ammonium and carboxylic acid functional groups. The term "alpha amino acid" as used herein denotes such a compound, wherein the quaternary ammonium is bonded directly to the alpha carbon, that is further substituted with a side chain consisting of an alkyl optionally substituted with one or more hydroxyl groups. Particular such alpha amino acids are those wherein the side chain is a linear $(C_1-C_8)$alkyl, such as methyl, ethyl, n-propyl and n-butyl, optionally substituted with one or more —OH groups.

In certain embodiments, the active agent comprised within the pharmaceutical composition of the present invention is a compound of the formula I, wherein $R_1$ is $(C_{15}-C_{21})$alkyl, or $(C_{15}-C_{21})$alkenyl having one or more, e.g., two, three, four, five or six, double bonds. Particular such embodiments are those wherein $R_1$ is a linear $(C_{15})$alkyl, $(C_{17})$alkenyl, $(C_{19})$alkenyl, or $(C_{21})$alkenyl. In more particular such embodiments, $R_1$ is $CH_3$—$(CH_2)_{14}$—, $CH_3$—$(CH_2)_7$—CH=CH—$(CH_2)_7$—, $CH_3$—$(CH_2)_4$—(CH=CH—$CH_2)_2$—$(CH_2)_6$—, $CH_3$—$(CH_2$—CH=CH$)_3$—$(CH_2)_7$—, $CH_3$—$(CH_2)_4$—(CH=CH—$CH_2)_4$—$(CH_2)_2$—, $CH_3$—$(CH_2$—CH=CH$)_5$—$(CH_2)_3$—, or $CH_3$—$(CH_2$—CH=CH$)_6$—$(CH_2)_2$—, and together with the carbonyl group attached thereto forms a palmitic acid residue, oleic acid reside, linoleic acid residue, linolenic acid residue, arachidonic acid residue, EPA residue, or DHA residue, respectively.

In certain embodiments, the active agent comprised within the pharmaceutical composition of the present invention is a compound of the formula I, wherein $R_2$ is —O—$CH_2$—$CHR_4$—$CH_2$—O—, —NH—$CH_2$—$CHR_4$—$CH_2$—O—, —O—, or —NH—, wherein $R_4$ is —OH, or —O—C(O)—$R_6$. Particular such embodiments are those wherein $R_4$ is —OH.

In certain embodiments, the active agent comprised within the pharmaceutical composition of the present invention is a compound of the formula I, wherein $R_3$ is a linear $(C_1-C_8)$alkylene substituted, preferably at the carbon atom attached to the carboxyl group, with a group of the formula —$N^+(R_5)_3$, i.e., —$(CH_2)_{1-7}$—$CH(N^+(R_5)_3)$—, that is optionally further substituted with one or more —OH groups.

In certain embodiments, the active agent comprised within the pharmaceutical composition of the present invention is a compound of the formula I, wherein $R_5$ each independently is $(C_1-C_4)$alkyl, e.g., methyl, ethyl, n-propyl, or isopropyl.

In certain embodiments, the active agent comprised within the pharmaceutical composition of the present invention is a compound of the formula I, wherein $R_6$ is $(C_{15}-C_{21})$alkyl, or $(C_{15}-C_{21})$alkenyl having one or more, e.g., two, three, four, five or six, double bonds. Particular such embodiments are those wherein $R_6$ is a linear $(C_{15})$alkyl, $(C_{17})$alkenyl, $(C_{19})$alkenyl, or $(C_{21})$alkenyl. In more particular such embodiments, $R_6$ is $CH_3$—$(CH_2)_{14}$—, $CH_3$—$(CH_2)_7$—CH=CH—$(CH_2)_7$—, $CH_3$—$(CH_2)_4$—(CH=CH—$CH_2)_2$—$(CH_2)_6$—, $CH_3$—$(CH_2$—CH=CH$)_3$—$(CH_2)_7$—, $CH_3$—$(CH_2)_4$—(CH=CH—$CH_2)_4$—$(CH_2)_2$—, $CH_3$—$(CH_2$—CH=CH$)_5$—$(CH_2)_3$—, or $CH_3$—$(CH_2$—CH=CH$)_6$—$(CH_2)_2$—, and together with the carbonyl group attached thereto forms a palmitic acid residue, oleic acid reside, linoleic acid residue, linolenic acid residue, arachidonic acid residue, EPA residue, or DHA residue, respectively.

In certain embodiments, the active agent comprised within the pharmaceutical composition of the present invention is a compound of the formula I, wherein $R_1$ is $(C_{15}-C_{21})$alkyl, or $(C_{15}-C_{21})$alkenyl having one or more double bonds, preferably a linear $(C_{15})$alkyl, $(C_{17})$alkenyl, $(C_{19})$alkenyl, or $(C_{21})$alkenyl; $R_2$ is —O—$CH_2$—$CHR_4$—$CH_2$—O—, —NH—$CH_2$—$CHR_4$—$CH_2$—O—, —O—, or —NH—; $R_3$ is —$(CH_2)_{1-7}$—$CH(N^+(R_5)_3)$—, optionally further substituted with one or more —OH groups; $R_4$ is —OH, or —O—C(O)—$R_6$; $R_5$ each independently is $(C_1-C_4)$alkyl such as methyl, ethyl, n-propyl, or isopropyl; and $R_6$ is $(C_{15}-C_{21})$alkyl, or $(C_{15}-C_{21})$alkenyl having one or more double bonds, preferably a linear $(C_{15})$alkyl, $(C_{17})$alkenyl, $(C_{19})$alkenyl, or $(C_{21})$alkenyl. In particular such embodiments, $R_1$ is $CH_3$—$(CH_2)_{14}$—, $CH_3$—$(CH_2)_7$—CH=CH—$(CH_2)_7$—, $CH_3$—$(CH_2)_7$—CH=CH—$(CH_2)_7$—, $CH_3$—$(CH_2)_4$—(CH=CH—$CH_2)_2$—$(CH_2)_6$—, $CH_3$—$(CH_2$—CH=CH$)_3$—$(CH_2)_7$—, $CH_3$—$(CH_2)_4$—(CH=CH—$CH_2)_4$—$(CH_2)_2$—, $CH_3$—$(CH_2$—CH=CH$)_5$—$(CH_2)_3$—, or $CH_3$—$(CH_2$—CH=CH$)_6$—$(CH_2)_2$—. More particular such embodiments are those wherein (i) $R_2$ is —O—$CH_2$—CHOH—$CH_2$—O—, $R_3$ is —$CH_2$—$CH(N^+(R_5)_3)$—, or —$(CH_2)_2$—$CH(N^+(R_5)_3)$—, forming together with the —O— and carboxyl group linked thereto either a serine or homoserine residue, respectively, in which the amino group is replaced by an ammonium cation; and $R_5$ each is methyl, ethyl, n-propyl, or isopropyl; (ii) $R_2$ is —NH—$CH_2$—CHOH—$CH_2$—O—; $R_3$ is —$CH_2$—$CH(N^+(R)_3)$—, or —$(CH_2)_2$—$CH(N^+(R_5)_3)$—, forming together with the —O— and carboxyl group linked thereto either a serine or homoserine residue, respectively, in which the amino group is replaced by an ammonium cation; and $R_5$ each is methyl, ethyl, n-propyl, or isopropyl; (iii) $R_2$ is —O—; $R_3$ is —$CH_2$—$CH(N^+(R_5)_3)$—, or —$(CH_2)_2$—$CH(N^+(R_5)_3)$—, forming together with the —O— and carboxyl group linked thereto either a serine or homoserine residue, respectively, in which the amino group is replaced by an ammonium cation; and $R_5$ each is methyl, ethyl, n-propyl, or isopropyl; or (iv) $R_2$ is —NH—; $R_3$ is —$CH_2$—$CH(N^+(R_5)_3)$—, or —$(CH_2)_2$—$CH(N^+(R_5)_3)$—, forming together with the —NH— and carboxyl group linked thereto, a 2,3-diaminopropanoic acid or 2,3-diaminobutyric acid residue, respectively, in which the amino group linked to the carbon atom at position 2 is replaced by an ammonium cation; and $R_5$ each is methyl, ethyl, n-propyl, or isopropyl.

In certain specific such embodiments, the active agent comprised within the pharmaceutical composition of the present invention is a compound of the formula Ia, wherein (i) $R_1$ is $CH_3$—$(CH_2)_{14}$—; $R_2$ is —O—$CH_2$—CHOH—$CH_2$—O—; and $R_3$ is —$CH_2$—$CH(N^+(R_5)_3)$— or —$(CH_2)_2$—$CH(N^+(R_5)_3)$—, herein identified compound Ia-1 and Ia-2, respectively; (ii) $R_1$ is $CH_3$—$(CH_2)_7$—CH=CH—$(CH_2)_7$—; $R_2$ is —O—$CH_2$—CHOH—$CH_2$—O—; and $R_3$ is —$CH_2$—$CH(N^+(R_5)_3)$— or —$(CH_2)_2$—$CH(N^+(R_5)_3)$—, herein identified compound Ia-3 and Ia-4, respectively; (iii) $R_1$ is $CH_3$—$(CH_2)_4$—(CH=CH—$CH_2)_2$—$(CH_2)_6$—; $R_2$ is —O—$CH_2$—CHOH—$CH_2$—O—; and $R_3$ is —$CH_2$—$CH(N^+(R_5)_3)$— or —$(CH_2)_2$—$CH(N^+(R_5)_3)$—, herein identified compound Ia-5 and Ia-6, respectively; (iv) $R_1$ is $CH_3$—$(CH_2$—CH=CH$)_3$—$(CH_2)_7$—; $R_2$ is —O—$CH_2$—CHOH—$CH_2$—O—; and $R_3$ is —$CH_2$—$CH(N^+(R_5)_3)$— or —$(CH_2)_2$ —CH(N⁺(R₅)₃)—, herein identified compound Ia-7 and Ia-8, respectively; (v) R₁ is CH₃—(CH₂)₄—(CH═CH—CH₂)₄—(CH₂)₂—; R₂ is —O—CH₂—CHOH—CH₂—O—; and R₃ is —CH₂—CH(N⁺(R₅)₃)— or —(CH₂)₂—CH(N⁺(R₅)₃)—, herein identified compound Ia-9 and Ia-10, respectively; (vi) R₁ is CH₃—(CH₂—CH═CH)₅—(CH₂)₃—; R₂ is —O—CH₂—CHOH—CH₂—O—; and R₃ is —CH₂—CH(N⁺(R₅)₃)— or —(CH₂)₂—CH(N⁺(R₅)₃)—, herein identified compound Ia-11 and Ia-12 (lyso-DGTS, when n is 2; and R₅ is methyl), respectively; or (vii) R₁ is CH₃—(CH₂—CH═CH)₆—(CH₂)₂—; R₂ is —O—CH₂—CHOH—CH₂—O—; and R₃ is —CH₂—CH(N⁺(R)₃)— or —(CH₂)₂—CH(N⁺(R₅)₃)—, herein identified compound Ia-13 and Ia-14, respectively. In all these compounds, R₅ can be either methyl or ethyl (Table 2).

In other specific such embodiments, the active agent comprised within the pharmaceutical composition of the present invention is a compound of the formula Ib, wherein (i) R₁ is CH₃—(CH₂)₁₄—; R₂ is —NH—CH₂—CHOH—CH₂—O—; and R₃ is —CH₂—CH(N⁺(R₅)₃)— or —(CH₂)₂—CH(N⁺(R₅)₃)—, herein identified compound Ib-1 and Ib-2, respectively; (ii) R₁ is CH₃—(CH₂)₇—CH═CH—(CH₂)₇—; R₂ is —NH—CH₂—CHOH—CH₂—O—; and R₃ is —CH₂—CH(N⁺(R₅)₃)— or —(CH₂)₂—CH(N⁺(R₅)₃)—, herein identified compound Ib-3 and Ib-4, respectively; (iii) R₁ is CH₃—(CH₂)₄—(CH═CH—CH₂)₂—(CH₂)₆—; R₂ is —NH—CH₂—CHOH—CH₂—O—; and R₃ is —CH₂—CH(N⁺(R)₃)— or —(CH₂)₂—CH(N⁺(R₅)₃)—, herein identified compound Ib-5 and Ib-6, respectively; (iv) R₁ is CH₃—(CH₂—CH═CH)₃—(CH₂)₇—; R₂ is —NH—CH₂—CHOH—CH₂—O—; and R₃ is —CH₂—CH(N⁺(R₅)₃)— or —(CH₂)₂—CH(N⁺(R₅)₃)—, herein identified compound Ib-7 and Ib-8, respectively; (v) R₁ is CH₃—(CH₂)₄—(CH═CH—CH₂)₄—(CH₂)₂—; R₂ is —NH—CH₂—CHOH—CH₂—O—; and R₃ is —CH₂—CH(N⁺(R₅)₃)— or —(CH₂)₂—CH(N⁺(R₅)₃)—, herein identified compound Ib-9 and Ib-10, respectively; (vi) R₁ is CH₃—(CH₂—CH═CH)₅—(CH₂)₃—; R₂ is —NH—CH₂—CHOH—CH₂—O—; and R₃ is —CH₂—CH(N⁺(R₅)₃)— or —(CH₂)₂—CH(N⁺(R₅)₃)—, herein identified compound Ib-11 and Ib-12, respectively; or (vii) R₁ is CH₃—(CH₂—CH═CH)₆—(CH₂)₂—; R₂ is —NH—CH₂—CHOH—CH₂—O—; and R₃ is —CH₂—CH(N⁺(R₅)₃)— or —(CH₂)₂—CH(N⁺(R₅)₃)—, herein identified compound Ib-13 and Ib-14, respectively. In all these compounds, R₅ can be either methyl or ethyl (Table 2).

TABLE 2

Specific compounds of the formulas Ia and Ib described herein*

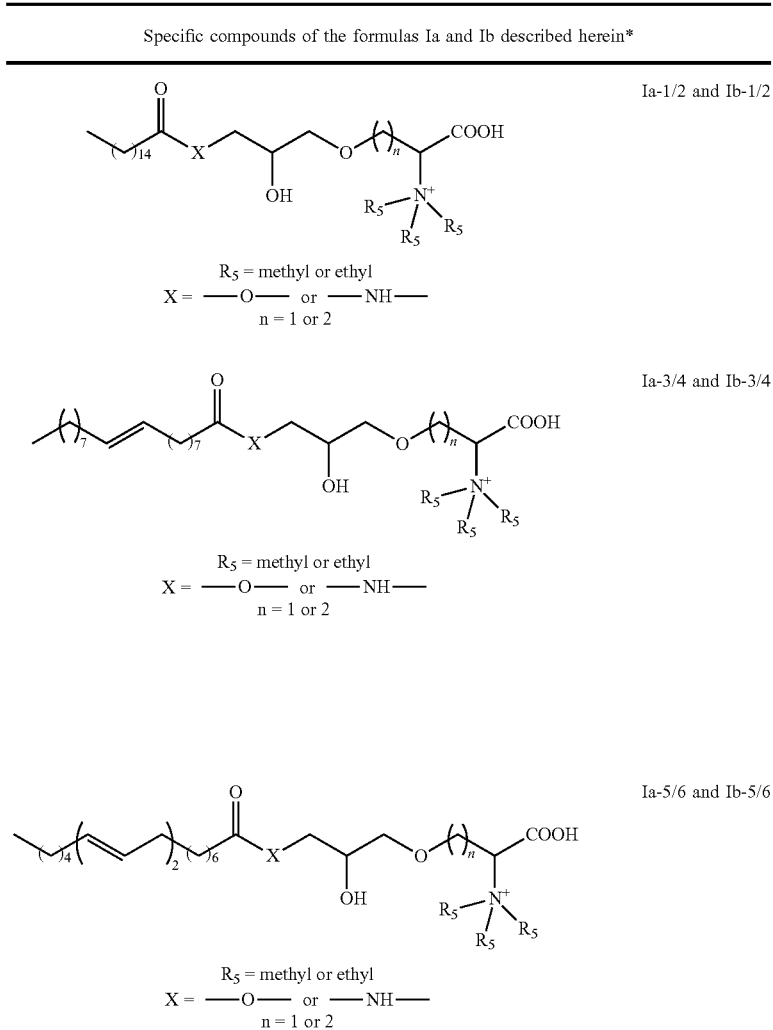

TABLE 2-continued

Specific compounds of the formulas Ia and Ib described herein*

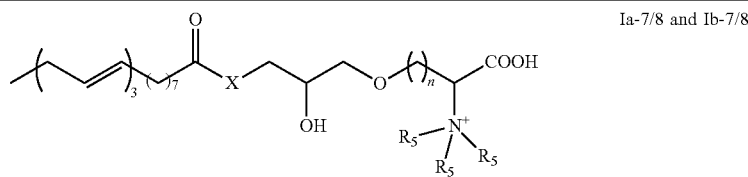

Ia-7/8 and Ib-7/8

$R_5$ = methyl or ethyl
X = —O— or —NH—
n = 1 or 2

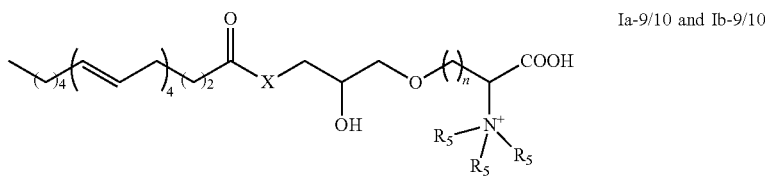

Ia-9/10 and Ib-9/10

$R_5$ = methyl or ethyl
X = —O— or —NH—
n = 1 or 2

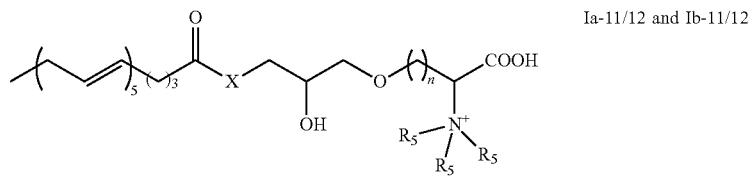

Ia-11/12 and Ib-11/12

$R_5$ = methyl or ethyl
X = —O— or —NH—
n = 1 or 2

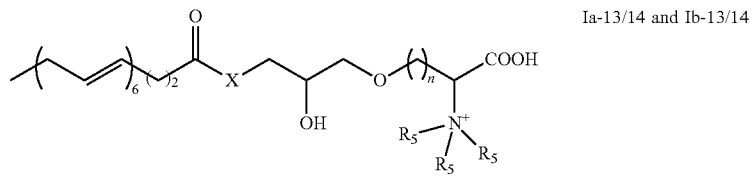

Ia-13/14 and Ib-13/14

$R_5$ = methyl or ethyl
X = —O— or —NH—
n = 1 or 2

*Compounds wherein $R_5$ is methyl are also referred to herein as Ia-1(methyl) to Ia-14(methyl), or Ib-1(methyl) to Ib-14(methyl); and compounds wherein $R_5$ is ethyl are also referred to herein as Ia-1(ethyl) to Ia-14(ethyl), or Ib-1(ethyl) to Ib-14(ethyl).

In yet other specific such embodiments, the active agent comprised within the pharmaceutical composition of the present invention is a compound of the formula Ic, wherein (i) $R_1$ is $CH_3$—$(CH_2)_{14}$—; $R_2$ is —O—; and $R_3$ is —$CH_2$—$CH(N^+(R)_3)$— or —$(CH_2)_2$—$CH(N^+(R_5)_3)$—, herein identified compound Ic-1 and Ic-2, respectively; (ii) $R_1$ is $CH_3$—$(CH_2)_7$—CH=CH—$(CH_2)_7$—; $R_2$ is —O—; and $R_3$ is —$CH_2$—$CH(N^+(R)_3)$— or —$(CH_2)_2$—$CH(N^+(R_5)_3)$—, herein identified compound Ic-3 and Ic-4, respectively; (iii) $R_1$ is $CH_3$—$(CH_2)_4$—(CH=CH—$CH_2)_2$—$(CH_2)_6$—; $R_2$ is —O—; and $R_3$ is —$CH_2$—$CH(N^+(R_5)_3)$— or —$(CH_2)_2$—$CH(N^+(R_5)_3)$—, herein identified compound Ic-5 and Ic-6, respectively; (iv) $R_1$ is $CH_3$—$(CH_2$—CH=CH)_3—$(CH_2)_7$—; $R_2$ is —O—; and $R_3$ is —$CH_2$—$CH(N^+(R)_3)$— or —$(CH_2)_2$—$CH(N^+(R_5)_3)$—, herein identified compound Ic-7 and Ic-8, respectively; (v) $R_1$ is $CH_3$—$(CH_2)_4$—(CH=CH—$CH_2)_4$—$(CH_2)_2$—; $R_2$ is —O—; and $R_3$ is —$CH_2$—$CH(N^+(R_5)_3)$— or —$(CH_2)_2$—$CH(N^+(R_5)_3)$—, herein identified compound Ic-9 and Ic-10, respectively; (vi) $R_1$ is $CH_3$—$(CH_2$—CH=CH)_5—$(CH_2)_3$—; $R_2$ is —O—; and $R_3$ is —$CH_2$—$CH(N^+(R_5)_3)$— or —$(CH_2)_2$—$CH(N^+(R_5)_3)$—, herein identified compound Ic-11 and Ic-12, respectively; or (vii) $R_1$ is $CH_3$—$(CH_2$—CH=CH)_6—$(CH_2)_2$—; $R_2$ is —O—; and $R_3$ is —$CH_2$—$CH(N^+(R_5)_3)$— or —$(CH_2)_2$—$CH(N^+(R_5)_3)$—, herein identified compound Ic-13 and Ic-14, respectively. In all these compounds, $R_5$ can be either methyl or ethyl (Table 3).

In still other specific such embodiments, the active agent comprised within the pharmaceutical composition of the present invention is a compound of the formula Id, wherein (i) $R_1$ is $CH_3$—$(CH_2)_{14}$—; $R_2$ is —NH—; and $R_3$ is —$CH_2$—$CH(N^+(R_5)_3)$— or —$(CH_2)_2$—$CH(N^+(R_5)_3)$—, herein identified compound Id-1 and Id-2, respectively; (ii) $R_1$ is $CH_3$—$(CH_2)_7$—CH=CH—$(CH_2)_7$—; $R_2$ is —NH—; and $R_3$ is —$CH_2$—$CH(N^+(R)_3)$— or —$(CH_2)_2$—$CH(N^+(R_5)_3)$—, herein identified compound Id-3 and Id-4, respectively; (iii) $R_1$ is $CH_3-(CH_2)_4-(CH=CH-CH_2)_2-(CH_2)_6-$; $R_2$ is $-NH-$; and $R_3$ is $-CH_2-CH(N^+(R)_3)-$ or $-(CH_2)_2-CH(N^+(R_5)_3)-$, herein identified compound Id-5 and Id-6, respectively; (iv) $R_1$ is $CH_3-(CH_2-CH=CH)_3-(CH_2)_7-$; $R_2$ is $-NH-$; and $R_3$ is $-CH_2-CH(N^+(R)_3)-$ or $-(CH_2)_2-CH(N^+(R_5)_3)-$, herein identified compound Id-7 and Id-8, respectively; (v) $R_1$ is $CH_3-(CH_2)_4-(CH=CH-CH_2)_4-(CH_2)_2-$; $R_2$ is $-NH-$; and $R_3$ is $-CH_2-CH(N^+(R)_3)-$ or $-(CH_2)_2-CH(N^+(R_5)_3)-$, herein identified compound Id-9 and Id-10, respectively; (vi) $R_1$ is $CH_3-(CH_2-CH=CH)_5-(CH_2)_3-$; $R_2$ is $-NH-$; and $R_3$ is $-CH_2-CH(N^+(R)_3)-$ or $-(CH_2)_2-CH(N^+(R_5)_3)-$, herein identified compound Id-11 and Id-12, respectively; or (vii) $R_1$ is $CH_3-(CH_2-CH=CH)_6-(CH_2)_2-$; $R_2$ is $-NH-$; and $R_3$ is $-CH_2-CH(N^+(R_5)_3)-$ or $-(CH_2)_2-CH(N^+(R_5)_3)-$, herein identified compound Id-13 and Id-14, respectively. In all these compounds, $R_5$ can be either methyl or ethyl (Table 3).

TABLE 3

Specific compounds of the formulas Ic and Id described herein*

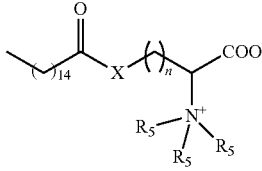

Ic-1/2 and Id-1/2

$R_5$ = methyl or ethyl
X = $-O-$ or $-NH-$
n = 1 or 2

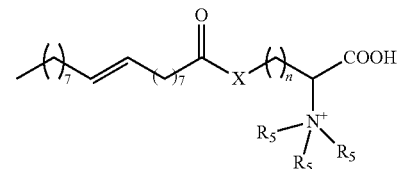

Ic-3/4 and Id-3/4

$R_5$ = methyl or ethyl
X = $-O-$ or $-NH-$
n = 1 or 2

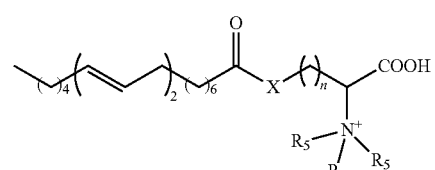

Ic-5/6 and Id-5/6

$R_5$ = methyl or ethyl
X = $-O-$ or $-NH-$
n = 1 or 2

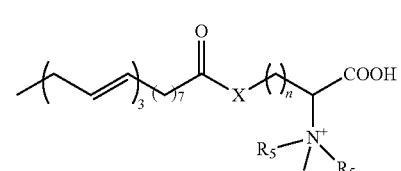

Ic-7/8 and Id-7/8

$R_5$ = methyl or ethyl
X = $-O-$ or $-NH-$
n = 1 or 2

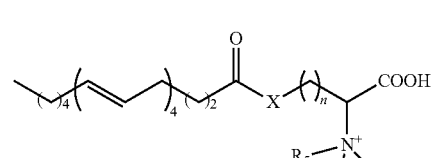

Ic-9/10 and Id-9/10

$R_5$ = methyl or ethyl
X = $-O-$ or $-NH-$
n = 1 or 2

TABLE 3-continued

Specific compounds of the formulas Ic and Id described herein*

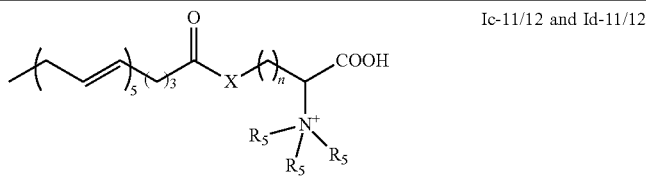

Ic-11/12 and Id-11/12

R$_5$ = methyl or ethyl
X = —O— or —NH—
n = 1 or 2

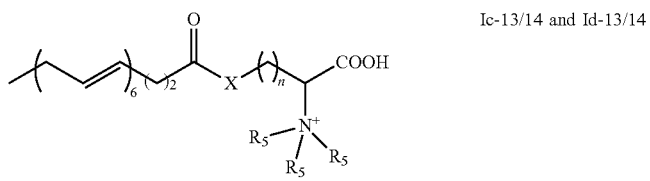

Ic-13/14 and Id-13/14

R$_5$ = methyl or ethyl
X = —O— or —NH—
n = 1 or 2

*Compounds wherein R$_5$ is methyl are also referred to herein as Ic-1(methyl) to Ic-14(methyl), or Id-1(methyl) to Id-14(methyl); and compounds wherein R$_5$ is ethyl are also referred to herein as Ic-1(ethyl) to Ic-14(ethyl), or Id-1(ethyl) to Id-14(ethyl).

The compounds of the formula I may be synthesized according to any technology or procedure known in the art, e.g., as described in the Examples section and depicted in Schemes 1-4 hereinafter.

The pharmaceutical compositions of the present invention can be provided in a variety of formulations, e.g., in a pharmaceutically acceptable form and/or in a salt or solvate form, as well as in a variety of dosages.

In one embodiment, the pharmaceutical composition of the present invention comprises a salt of a compound of the formula I with a non-toxic pharmaceutically acceptable anion. Pharmaceutically acceptable anions include, without being limited to, the hydrochloride salt, the hydrobromide salt, the hydroiodide salt, the acetate, mesylate, esylate, maleate, fumarate, tartrate, bitartrate, sulfate, p-toluenesulfonate, benzenesulfonate, methanesulfonate, ethanedisulfonate (edisylate), ethanesulfonate (esylate), tosylate, benzoate, acetate, phosphate, carbonate, bicarbonate, succinate, and citrate. Multiple pharmaceutically acceptable anions can be used in a single preparation if desired.

Pharmaceutically acceptable salts of the compound of the formula I may be formed by conventional means, e.g., by reacting the free base form of the active agent with one or more equivalents of the appropriate acid in a solvent or medium in which the salt is insoluble, or in a solvent such as water which is removed in vacuo or by freeze drying, or by exchanging the anions of an existing salt for another anion on a suitable ion exchange resin.

The pharmaceutical compositions provided by the present invention may be prepared by conventional techniques, e.g., as described in Remington: The Science and Practice of Pharmacy, 19$^{th}$ Ed., 1995. The compositions can be prepared, e.g., by uniformly and intimately bringing the active agent, i.e., the compound of the formula I, into association with a liquid carrier, a finely divided solid carrier, or both, and then, if necessary, shaping the product into the desired formulation. The compositions may be in liquid, solid or semisolid form and may further include pharmaceutically acceptable fillers, carriers, diluents or adjuvants, and other inert ingredients and excipients. In one embodiment, the pharmaceutical composition of the present invention is formulated as nanoparticles.

The compositions can be formulated for any suitable route of administration, including oral, rectal, nasal, intravenous, intraarterial, intramuscular, intraperitoneal, intrathecal, intrapleural, intratracheal, subcutaneous, transdermal, intradermal, vaginal, and topical administration, as well as for inhalation. The exact dosage and regimen of administration of the composition will be determined as deemed appropriate by the practitioner, and dependent upon the therapeutic effect to be achieved and may vary with the particular formula, the route of administration, and the age and condition of the individual subject to whom the composition is to be administered.

For parenteral administration, the pharmaceutical composition of the invention may be in the form of a sterile injectable aqueous or oleagenous suspension, which may be formulated according to the known art using suitable dispersing, wetting or suspending agents. The sterile injectable preparation may also be a sterile injectable solution or suspension in a non-toxic parenterally acceptable diluent or solvent. Acceptable vehicles and solvents that may be employed include, without limiting, water, Ringer's solution, polyethylene glycol (PEG), 2-hydroxypropyl-3-cyclodextrin (HPCD), Tween-80, and isotonic sodium chloride solution. The compositions may be presented in unit-dose or multi-dose containers, e.g., sealed vials and ampoules, and may be stored in a freeze-dried (lyophilized) condition requiring only the addition of sterile liquid carrier, e.g. water, prior to use.

For transdermal administration, e.g., gels, patches or sprays can be contemplated.

Pharmaceutical compositions according to the present invention, when formulated for inhalation, may be administered utilizing any suitable device known in the art, such as metered dose inhalers, liquid nebulizers, dry powder inhalers, sprayers, thermal vaporizers, electrohydrodynamic aerosolizers, and the like.

Pharmaceutical compositions according to the present invention, when formulated for administration route other than parenteral administration, may be in a form suitable for oral use, e.g., as tablets, troches, lozenges, aqueous, or oily suspensions, dispersible powders or granules, emulsions, hard or soft capsules, or syrups or elixirs.

Compositions intended for oral use may be prepared according to any method known to the art for the manufacture of pharmaceutical compositions and may further comprise one or more agents selected from sweetening agents, flavoring agents, coloring agents and preserving agents in order to provide pharmaceutically elegant and palatable preparations. Tablets contain the active agent(s) in admixture with non-toxic pharmaceutically acceptable excipients, which are suitable for the manufacture of tablets. These excipients may be, e.g., inert diluents such as calcium carbonate, sodium carbonate, lactose, calcium phosphate, or sodium phosphate; granulating and disintegrating agents, e.g., corn starch or alginic acid; binding agents, e.g., starch, gelatin or acacia; and lubricating agents, e.g., magnesium stearate, stearic acid, or talc. The tablets may be either uncoated or coated utilizing known techniques to delay disintegration and absorption in the gastrointestinal tract and thereby provide a sustained action over a longer period. For example, a time delay material such as glyceryl monostearate or glyceryl distearate may be employed. They may also be coated using the techniques described in the U.S. Pat. Nos. 4,256,108, 4,166,452 and 4,265,874 to form osmotic therapeutic tablets for control release. The pharmaceutical composition of the invention may also be in the form of oil-in-water emulsion.

The pharmaceutical compositions of the invention may be formulated for controlled release of the active agent. Such compositions may be formulated as controlled-release matrix, e.g., as controlled-release matrix tablets in which the release of a soluble active agent is controlled by having the active diffuse through a gel formed after the swelling of a hydrophilic polymer brought into contact with dissolving liquid (in vitro) or gastro-intestinal fluid (in vivo). Many polymers have been described as capable of forming such gel, e.g., derivatives of cellulose, in particular the cellulose ethers such as hydroxypropyl cellulose, hydroxymethyl cellulose, methylcellulose or methyl hydroxypropyl cellulose, and among the different commercial grades of these ethers are those showing fairly high viscosity. In other configurations, the compositions comprise the active agent formulated for controlled release in microencapsulated dosage form, in which small droplets of the active agent are surrounded by a coating or a membrane to form particles in the range of a few micrometers to a few millimeters.

Another contemplated formulation is depot systems, based on biodegradable polymers, wherein as the polymer degrades, the active agent is slowly released. The most common class of biodegradable polymers is the hydrolytically labile polyesters prepared from lactic acid, glycolic acid, or combinations of these two molecules. Polymers prepared from these individual monomers include poly (D,L-lactide) (PLA), poly (glycolide) (PGA), and the copolymer poly (D,L-lactide-co-glycolide) (PLG).

In another aspect, the present invention relates to a compound of the formula I as defined in any one of the embodiments above, or a pharmaceutically acceptable salt or solvate thereof, for use in the inhibition/treatment of atherosclerotic cardiovascular disease. Particular such compounds are those specifically described herein, i.e., the compounds herein identified Ia-1 to Ia-14, Ib-1 to Ib-14, Ic-1 to Ic-14, and Id-1 to Id-14 (in each case, $R_5$ may be either methyl or ethyl).

In yet another aspect, the present invention relates to use of a compound of the formula I as defined in any one of the embodiments above, or a pharmaceutically acceptable salt or solvate thereof, for the preparation of a pharmaceutical medicament for treatment of atherosclerotic cardiovascular disease. Particular such compounds are those specifically described herein, i.e., the compounds herein identified Ia-1 to Ia-14, Ib-1 to Ib-14, Ic-1 to Ic-14, and Id-1 to Id-14 (in each case, $R_5$ may be either methyl or ethyl).

In still another aspect, the present invention relates to a method for treatment of atherosclerotic cardiovascular disease in a subject in need thereof, comprising administering to said subject a therapeutically effective amount of a compound of the formula I as defined in any one of the embodiments above, or a pharmaceutically acceptable salt or solvate thereof. Particular such compounds are those specifically described herein, i.e., the compounds herein identified Ia-1 to Ia-14, Ib-1 to Ib-14, Ic-1 to Ic-14, and Id-1 to Id-14 (in each case, $R_5$ may be either methyl or ethyl).

The term "treatment" as used herein refers to the administering of a therapeutic amount of an active agent, i.e., a compound of the formula I as defined herein, which is effective to ameliorate undesired symptoms associated with the medical condition treated, i.e., atherosclerotic cardiovascular disease; prevent the manifestation of such symptoms before they occur; slow down the progression of said medical condition; slow down the deterioration of symptoms; enhance the onset of remission period; slow down the irreversible damage caused in the progressive chronic stage of said medical condition; delay the onset of said progressive stage; lessen the severity or cure said medical condition; improve survival rate or more rapid recovery; and/or prevent said medical condition form occurring.

The term "effective amount" as used herein means an amount of an active agent that will elicit the biological or medical response of a tissue, system, animal or human that is being sought. The amount must be effective to achieve the desired therapeutic effect as described above, depending, inter alia, on the type and severity of the medical condition to be treated and the treatment regime. The effective amount is typically determined in appropriately designed clinical trials (dose range studies) and the person versed in the art will know how to properly conduct such trials to determine the effective amount. As generally known, an effective amount depends on a variety of factors including the distribution profile of the active agent within the body, a variety of pharmacological parameters such as half-life in the body, on undesired side effects, if any, on factors such as age and gender, etc.

The term "subject" as used herein refers to any mammal, e.g., a human, non-human primate, horse, ferret, dog, cat, cow, and goat. In a preferred embodiment, the term "subject" denotes a human, i.e., an individual.

In a further aspect, the present invention provides a compound of the formula I as defined in any one of the embodiments above, but excluding the compounds wherein $R_2$ is —O—$CH_2$—$CHR_4$—$CH_2$—O—, i.e., a compound of the formula Ib wherein $R_2$ is —NH—$CH_2$—$CHR_4$—$CH_2$—O—; of the formula Ic wherein $R_2$ is —O—; or of the formula Id wherein $R_2$ is —NH—.

In certain embodiments, the compound of the present invention is a compound of the formula I, wherein $R_1$ is $(C_{15}$-$C_{21})$alkyl, or $(C_{15}$-$C_{21})$alkenyl having one or more, e.g., two, three, four, five or six, double bonds. Particular such embodiments are those wherein $R_1$ is a linear $(C_{15})$ alkyl, $(C_{17})$alkenyl, $(C_{19})$alkenyl, or $(C_{21})$alkenyl. In more particular such embodiments, $R_1$ is $CH_3$—$(CH_2)_{14}$—, $CH_3$—$(CH_2)_7$—$CH$=$CH$—$(CH_2)_7$—, $CH_3$—$(CH_2)_4$—$(CH$=$CH$—$CH_2)_2$—$(CH_2)_6$—, $CH_3$—$(CH_2$—$CH$=$CH)_3$—$(CH_2)_7$—, $CH_3$—$(CH_2)_4$—$(CH$=$CH$—$CH_2)_4$—$(CH_2)_2$—, $CH_3$—$(CH_2$—$CH$=$CH)_5$—$(CH_2)_3$—, or $CH_3$—$(CH_2$—$CH$=$CH)_6$—$(CH_2)_2$—, and together with the carbonyl group attached thereto forms a palmitic acid residue, oleic acid reside, linoleic acid residue, linolenic acid residue, arachidonic acid residue, EPA residue, or DHA residue, respectively.

In certain embodiments, the compound of the present invention is a compound of the formula I, wherein $R_2$ is —NH—$CH_2$—$CHR_4$—$CH_2$—O—, —O—, or —NH—, wherein $R_4$ is —OH.

In other embodiments, the compound of the present invention is a compound of the formula I, wherein $R_2$ is —NH—$CH_2$—$CHR_4$—$CH_2$—O—, wherein $R_4$ is —O—C(O)—$R_6$, or —NH—C(O)—$R_6$. In particular such embodiments, $R_6$ is $(C_{15}$-$C_{21})$alkyl, or $(C_{15}$-$C_{21})$alkenyl having one or more double bonds, e.g., a linear $(C_{15})$alkyl, $(C_{17})$alkenyl, $(C_{19})$alkenyl, or $(C_{21})$alkenyl. In more particular such embodiments, $R_6$ is $CH_3$—$(CH_2)_{14}$—, $CH_3$—$(CH_2)_7$—$CH$=$CH$—$(CH_2)_7$—, $CH_3$—$(CH_2)_4$—$(CH$=$CH$—$CH_2)_2$—$(CH_2)_6$—, $CH_3$—$(CH_2$—$CH$=$CH)_3$—$(CH_2)_7$—, $CH_3$—$(CH_2)_4$—$(CH$=$CH$—$CH_2)_4$—$(CH_2)_2$—, $CH_3$—$(CH_2$—$CH$=$CH)_5$—$(CH_2)_3$—, or $CH_3$—$(CH_2$—$CH$=$CH)_6$—$(CH_2)_2$—, and together with the carbonyl group attached thereto forms a palmitic acid residue, oleic acid reside, linoleic acid residue, linolenic acid residue, arachidonic acid residue, EPA residue, or DHA residue, respectively.

In certain embodiments, the compound of the present invention is a compound of the formula I, wherein $R_3$ is a linear $(C_1$-$C_8)$alkylene substituted, preferably at the carbon atom attached to the carboxyl group, with a group of the formula —$N^+(R_5)_3$, i.e., —$(CH_2)_{1-7}$—$CH(N^+(R_5)_3)$—, that is optionally further substituted with one or more —OH groups.

In certain embodiments, the compound of the present invention is a compound of the formula I, wherein $R_5$ each independently is $(C_1$-$C_4)$alkyl, e.g., methyl, ethyl, n-propyl, or isopropyl.

In certain embodiments, the compound of the present invention is a compound of the formula I, wherein (i) $R_1$ is $(C_{15}$-$C_{21})$alkyl, or $(C_{15}$-$C_{21})$alkenyl having one or more double bonds, preferably a linear $(C_{15})$alkyl, $(C_{17})$alkenyl, $(C_{19})$alkenyl, or $(C_{21})$alkenyl; (ii) $R_2$ is —NH—$CH_2$—$CHR_4$—$CH_2$—O—, —O—, or —NH—, wherein $R_4$ is —OH; (iii) $R_3$ is —$(CH_2)_{1-7}$—$CH(N^+(R_5)_3)$—, optionally further substituted with one or more —OH groups; and (iv) $R_5$ each independently is $(C_1$-$C_4)$alkyl such as methyl, ethyl, n-propyl, or isopropyl.

In particular such embodiments, the compound of the present invention is a compound of the formula I, wherein $R_1$ is $CH_3$—$(CH_2)_{14}$—, $CH_3$—$(CH_2)_7$—$CH$=$CH$—$(CH_2)_7$—, $CH_3$—$(CH_2)_4$—$(CH$=$CH$—$CH_2)_2$—$(CH_2)_6$—, $CH_3$—$(CH_2$—$CH$=$CH)_3$—$(CH_2)_7$—, $CH_3$—$(CH_2)_4$—$(CH$=$CH$—$CH_2)_4$—$(CH_2)_2$—, $CH_3$—$(CH_2$—$CH$=$CH)_5$—$(CH_2)_3$—, or $CH_3$—$(CH_2$—$CH$=$CH)_6$—$(CH_2)_2$—. More particular such embodiments are those wherein (i) $R_2$ is —NH—$CH_2$—CHOH—$CH_2$—O—, $R_3$ is —$CH_2$—$CH(N^+(R_5)_3)$—, or —$(CH_2)_2$—$CH(N^+(R_5)_3)$—, forming together with the —O— and carboxyl group linked thereto either a serine or homoserine residue, respectively, in which the amino group is replaced by an ammonium cation; and $R_5$ each is methyl, ethyl, n-propyl, or isopropyl; (ii) $R_2$ is —O—; $R_3$ is —$CH_2$—$CH(N^+(R_5)_3)$—, or —$(CH_2)_2$—$CH(N^+(R_5)_3)$—, forming together with the —O— and carboxyl group linked thereto either a serine or homoserine residue, respectively, in which the amino group is replaced by an ammonium cation; and $R_5$ each is methyl, ethyl, n-propyl, or isopropyl; or (iii) $R_2$ is —NH—; $R_3$ is —$CH_2$—$CH(N^+(R_5)_3)$—, or —$(CH_2)_2$—$CH(N^+(R_5)_3)$—, forming together with the —NH— and carboxyl group linked thereto, a 2,3-diaminopropanoic acid or 2,3-diaminobutyric acid residue, respectively, in which the amino group Inked to the carbon atom at position 2 is replaced by an ammonium cation; and $R_5$ each is methyl, ethyl, n-propyl, or isopropyl.

In specific such embodiments, the compound of the present invention is a compound of the formula Ib, Ic or Id, selected from the compounds herein identified Ib-1 to Ib-14, Ic-1 to Ic-14, and Id-1 to Id-14 (in each case, $R_5$ may be either methyl or ethyl).

In yet a further aspect, the present invention provides a pharmaceutical composition comprising a compound of the formula I as defined in any one of the embodiments above, but excluding the compounds wherein $R_2$ is —O—$CH_2$—$CHR_4$—$CH_2$—O—, or a pharmaceutically acceptable salt or solvate thereof, and a pharmaceutically acceptable carrier. Particular such compounds are those specifically described herein, i.e., the compounds herein identified Ib-1 to Ib-14, Ic-1 to Ic-14, and Id-1 to Id-14 (in each case, $R_5$ may be either methyl or ethyl).

The invention will now be illustrated by the following non-limiting Examples.

EXAMPLES

Materials and Methods

Materials

Recombinant PON1 (rePON1), generated in *Escherichia coli* by direct evolution, was purchased from the Weizmann Institute of Science, Rehovot, Israel. Murine macrophage J774A.1 cells were purchased from the American Tissue Culture Collection (ATCC, Rockville, Md.). Penicillin, streptomycin, glutamine, nystatin, fetal calf serum (FCS), trypsin and XTT Cell Proliferation Assay Kit were purchased from Biological Industries (Bet-Haemek, Israel). Other buffers, solvents and reagents were purchased from Sigma-Aldrich. Human serum was purchased from Industries biologic (Bet-Haemk, Israel).

*Nannochloropsis* sp. microalgae as raw material in the form of freeze-dried powder was provided by Seambiotic, Israel. Lyso-DGTS was isolated from *Nannochloropsis* sp. Microalgae.

The Effect of Lyso-DGTS on rePON1 Activity

Incubation of Lyso-DGTS with rePON1.

To 200 μl of rePON1 solution (5 μg/ml) in Tris-HCl buffer pH=8.4 was added 1 μl of lyso-DGTS dissolved in dimethyl sulfoxide (DMSO) to a final concentration of 1, 5, 10, 50, and 100 μg/ml. 1 μl DMSO was added to the control rePON1 solution. The mixtures were incubated at 37° C. for 2, 4, 24 or 48 h.

Lactonase Activity.

10 μl from each solution were taken to a UV 96-well microplate containing 90 μl Tris-HCL buffer pH=8.4 with 1 mM $CaCl_2$ (activity buffer) in each well. Then 100 μl dihydrocoumarin, 2 mM in the activity buffer was added (prepared from a stock of 100 mM dihydrocoumarin in DMSO). Dihydrocoumarine hydrolysis rate was measured at 270 nm, once in 25 seconds for 15 minutes, using Spectra-Max M2 Reader. Non-enzymatic hydrolysis of dihydrocoumarin was subtracted from the total rate of hydrolysis. One unit of lactonase activity was equal to the hydrolysis of 1 µmol of dihydrocoumarin/min.

Esterase Activity.

10 µl from each solution were taken to a UV 96-well microplate wells containing 90 µl Tris-HCL buffer pH=8.4 with 1 mM $CaCl_2$ (activity buffer). Then 100 µl phenyl acetate, 2 mM in the activity buffer was added (prepared from a stock of 100 mM phenyl acetate in DMSO). Phenyl acetate hydrolysis rate was measured at 270 nm, once in 25 seconds, for 15 minutes using SpectraMax M2 Reader. One unit of esterase activity was equal to the hydrolysis of 1 µmol of phenyl acetate/min. Lactonase and esterase unit activity were calculated by the following equation:

$$\text{Unit}=\text{slope (mOD/min)} \times 5(\text{per ml}) \times 666.7(\text{dilution})/700.$$

Human Serum PON1 Lactonase Activity

200 µl of human serum diluted by 20 with phosphate-buffered saline (PBS) (PH=7.6) was incubated with lyso-DGTS at various concentrations (0, 1, 5, 10 and 50 µg/ml) for 4 h at 37° C. Then, 10 µl was taken to measure lactonase activity using the dihydrocoumarine assay.

Tryptophan Fluorescence-Quenching Measurements

To 200 µl rePON1 (50 µg/ml=1.16 µM) solution in black 96-well plate wells was added lyso-DGTS at various concentration (0, 1, 5, 10, 25, 50, 75, and 100 µg/ml). The solutions were incubated for 2 h at 25° C. or 37° C. Fluorescence measurements were performed with an Infinite M200 PRO fluorescence spectrophotometer (Tecan) with emission spectra recorded from 320 to 450 nm at an excitation wavelength of 290 nm.

Molecular Docking

The crystal structure of PON1 was retrieved from the Protein Data Bank (PDB). The enzyme was prepared for docking by the AutoDock Tools (ADT) program, an accessory program allowing the user to interact with AutoDock 4.2 from a graphic user interface. Water molecules were removed from the protein PDB file. Polar hydrogen atoms were added and Kollman united atom charges assigned. The solvation parameters were added by the Addsol program (part of the ADT program) and the grid points were set to 90, 90, 90; the spacing value equivalent to 0.375; and the grid center to X−10.4, Y−11.794, Z+30.00. Ligand-docking was carried out with the AutoDock 4.2 Genetic Algorithm (GA).

HDL and LDL Isolation

HDL and LDL were isolated from human plasma samples by discontinuous density gradient ultracentrifugation and dialyzed against saline containing sodium ethylenediaminetetraacetic acid (EDTA; 1 mmol/L) to protect the lipoproteins against oxidation. Before generating the experiments, LDL and HDL were dialyzed twice, for 1 h each time, and once more overnight against PBS at 4° C. to remove EDTA.

RePON1 Influx to J774A.1 Macrophages rePON1 (2 mg/ml) was reacted with fluorescein isothiocyanate (FITC) (200 µg/ml) for 1 h at 37° C. in the dark in borate buffer (PH=8.6). Glycine 10 mM was added and the solution was dialyzed using PBS buffer to remove FITC excess. RePON1-FITC conjugate (50 µg/ml) was incubated with lyso-DGTS at different concentration (10, 20, 50 and 100 µg/ml) into RPMI for 2 h. The solution was added to J774A.1 macrophages and incubated for 16 h. Cells were washed three times with sterile PBS buffer (0.1% sodium azid, 0.2% bovine serum albumin (BSA)), harvested in PBS (buffer) and analyzed by fluorescence-activated cell sorting (FACS) (Facscalibur 4ca). Results are presented as mean fluorescence intensity (MFI).

OxLDL-Induced Foam Cell Formation

J774A.1 macrophage cells were grown in RPMI 1640 media containing 10% FBS in cell culture flask till ~90% confluence (37° C. incubator containing 5% $CO_2$). The cells were incubated at 37° C. overnight under sterile conditions, approximately $1 \times 10^5$ J774.1 cells/well in a 96-well plate. Macrophage cells were incubated for an additional 24 h with lyso-DGTS (50 and 100 µg/ml), rePON1 (50 µg/ml), or rePON1 preincubated with different concentrations of lyso-DGTS (10, 20, 50 and 100 µg/ml). The cells were washed and ox-LDL (25 µg/ml in a RPMI medium) was added for another 24 h to yield foam cells. The cells were washed 3 times with PBS, following fixation with 4% formaldehyde for 10 min, the cells were stained with Oil Red O (0.35 mg/100 ml in 60% isopropanol; Sigma-Aldrich) for 15 min at 37° C. to evaluate the characteristic lipid accumulation in macrophage-derived foam cells. Foam cell formation was observed under microscope.

The density of lipid content was evaluated by alcohol extraction after staining. The absorbance at 514 nm was measured using microplate reader (Infinite M200 PRO fluorescence spectrophotometer (Tecan)).

HDL-Cholesterol Efflux

Cholesterol efflux Fluorometric Assay Kit (Cell-Based), Biovision was used to measure the effect of lyso-DGTS on HDL-cholesterol efflux.

J774.1 macrophage cells were grown in RPMI 1640 media containing 10% FBS in cell culture flask till ~90% confluence (37° C. incubator containing 5% $CO_2$). The cells were splitted under sterile conditions using basic cell culture techniques and plate to approximately $1 \times 10^5$ cells/well in a 96-well plate (white plate with clear bottom) using 100 µl media/well. After 2 h, the cells attached to the plates, washed with RPMI 1640 media (no serum added) and labeled with 50 µl labeling reagent and 50 µl equilibration buffer, supplied by the kit, for 16 h. 100 µl equilibration buffer alone were added to the background control for measuring background fluorescence. The cells were washed with media and treated for another 4-6 h with 100 µl of RPMI 1640 media containing HDL (25 µg protein) preincubated with lyso-DGTS at various concentrations (0, 10, 20, 50, and 100 µg/ml) for 4 h. To the negative control was added RPMI 1640 media alone.

The fluorescence of the supernatant was measured (excitation/emission=482/515 nm). The cells were solubilized adding 100 µl of Cell Lysis Buffer and shaking on a plate shaker for 30 min at room temperature, and its fluorescence was also measured.

Cholesterol efflux of the treatments was calculated by dividing the fluorescence intensity of the media by total fluorescence intensity of the cell lysate of the same treatment and media.

In-Vivo Experiment Using Balb/c Mice

Eight weeks old Balb/c mice where fed with normal rodent diet (the "non" group n=11) for 12 weeks or with high-fat diet (HFD) for 8 weeks. After 8 weeks, the HFD group was divided into two groups both treated via osmotic mini-pumps implanted subcutaneously: (1) vehicle group (the pumps contained 100 µl of DDW+2% Tween 80; n=9); (2) Lyso-DGTS group (the pumps contained 100 µl lyso-DGTS 1.4 mg/ml in DDW+2% Tween 80; n=1). The mice then continued with the same diet for another 4 weeks. The pumps injected 3.5 µl solution each day for 28 days until the end of the experiment. Blood was drawn and centrifuged at 2000 rpm for five minutes, and the serum was stored at −70° C. until the analyses. Clinical parameters were measured.

Serum diluted by 20 with PBS and PON1 lactonase activity was measured using dihydrocumarine assay.

Example 1. Effect of Lyso-DGTS on rePON1 Lactonase and Esterase Activities

The effect of lyso-DGTS on lactonase and arylesterase activities of rePON1 was examined. rePON1 (5 μg/ml in Tris buffer pH=8.4) was incubated with different concentrations of lyso-DGTS for 2, 4, 24, and 48 h at 37° C., and its lactonase and aryesterase activities were measured using dihydrocoumarin and phenyl acetate assays, respectively.

Incubation of rePON1 with lyso-DGTS increased enzyme lactonase activity in a dose dependent manner. The enzyme activity altered significantly from 3.00 units without lyso-DGTS to 4.05, 5.73, 8.10, 11.61, and 12.7 units at 1, 5, 10, 50, and 100 μg/ml lyso-DGTS, respectively, after 2 h of incubation (FIG. 1A).

Lactonase activity of rePON1 in buffer solution decreased with time and was abolished after 48 h, whereas the presence of lyso-DGTS stabilized and preserved protein lactonase activity for at least 48 h. Lyso-DGTS at 1, 5, 10, 50, and 100 μg/ml preserved rePON1 lactonase activity after incubation for 48 h by 9%, 33%, 49%, 69%, and 66%, respectively (FIG. 1A).

Figure 1B:
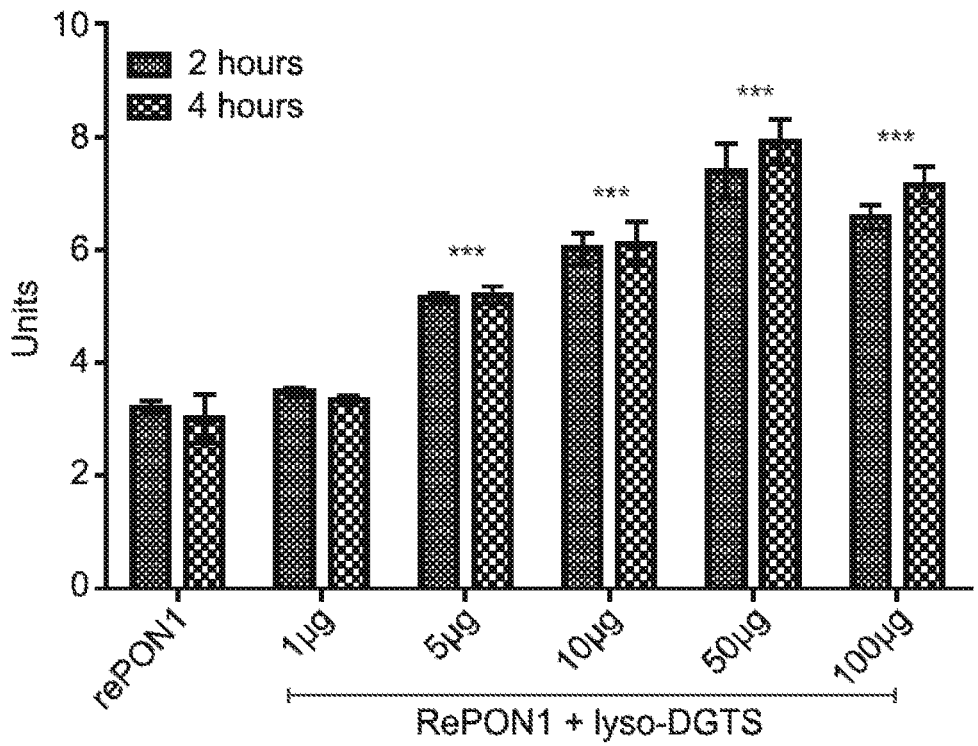

A similar effect was observed with/without lyso-DGTS incubated with rePON1 when arylesterase activity was monitored. However, in contrast to lactonase activity, aryl esterase activity of the enzyme remained stable after 4 h (FIG. 1B) and also after 24 h of incubation (data not shown).

Example 2. The Effect of Lyso-DGTS on Human Serum PON1 Lactonase Activity

Figure 2:
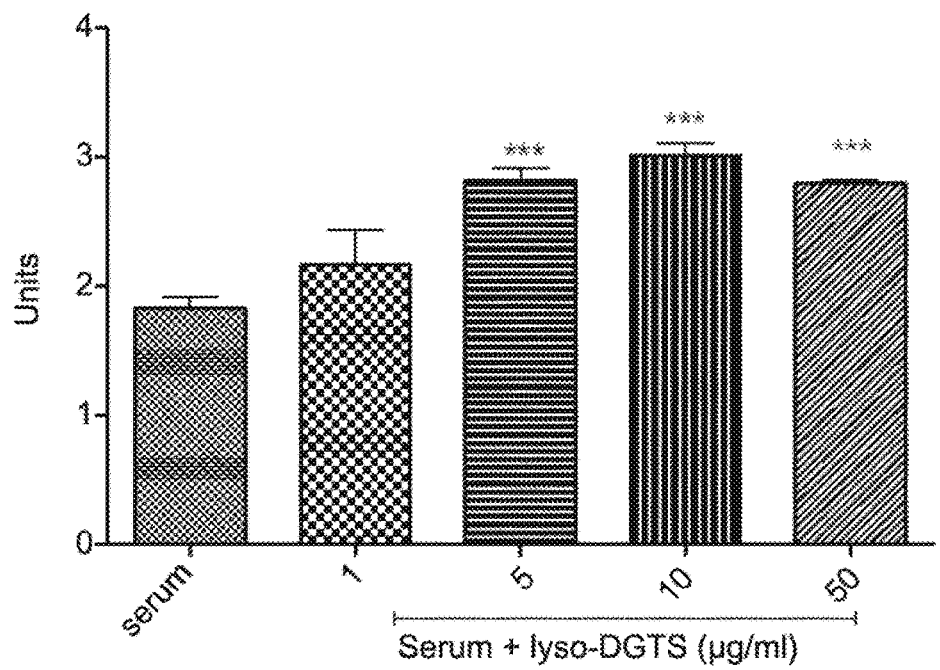
FIG. 2 shows human serum PON1 lactonase activity. Human serum was diluted by 20 with PBS and incubated with lyso-DGTS at a concentration of 0, 1, 5, 10, or 50 μg/ml for 4 h at 37° C. in Tris buffer pH=8.0, and PON1 lactonase activity was measured using dihydrocumarine assay. Each experiment was repeated separately at least three times. *$p<0.05$, ***$p<0.0001$ related to the control (serum without lyso-DGTS). Statistics were analyzed using one-way ANOVA and Graphpad prism 5 software.

The effect of lyso-DGTS on lactonase activity of human serum PON1 was examined. Human serum was diluted by 20 with PBS buffer and incubated with and without lyso-DGTS at concentrations of 1, 5, 10, and 50 μg/ml for 4 h at 37° C. Lactonase activity of the enzyme was measured using dihydrocoumarin assay. As shown in Example 1, lyso-DGTS increased human serum lactonase activity in a dose dependent manner up to 10 μg/ml, from 1.8 units without lyso-DGTS to 2.16, 2.82, 3.01, and 2.80 units at 1, 5, 10 and 50 μg/ml lyso-DGTS, respectively. The change at 1 μg/ml of lyso-DGTS was not statistically significant (FIG. 2).

Figure 3A:
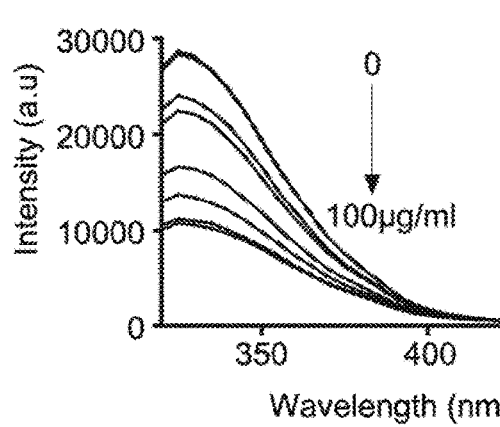
FIGS. 3A-3B show tryptophan fluorescence spectra of rePON1 (50 μg/ml; 1.16 μM) incubated with/without lyso-DGTS at concentrations of 1, 5, 10, 25, 50, 75, and 100 μg/ml in black 96-well plates for 2 h at 25° C. (3A) or 37° C. (3B). Fluorescence was measured at excitation of 290 nm and emission of 320-450 nm. Each experiment was repeated separately at least three times.
Figure 3B:
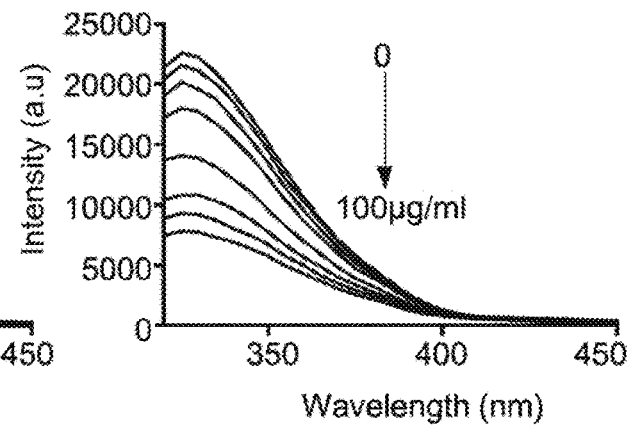

Example 3. rePON1-Lyso-DGTS Interaction Using Trp. Fluorescence Quenching Method The effect of lyso-DGTS on rePON1 can result from a specific interaction between the lipid and the enzyme which was studied using Trp fluorescence quenching method. FIG. 3 shows the emission spectra of rePON1 in the presence of various concentrations of lyso-DGTS at 25° C. (FIG. 3A) and 37° C. (FIG. 3B) in the 300-450 nm range with an excitation wavelength of 290 nm. Lyso-DGTS quenched the fluorescence of rePON1 in a dose dependent manner at both temperatures.

Quenching pathways can be described by the Stern-Volmer equation (eq. 1):

$$\frac{F0}{F} = 1 + Ksv[Q] \qquad \text{Eq. 1}$$

where F0 and F are the fluorescence intensities in the absence and presence of quencher (lyso-DGTS), respectively, Ksv is the Stern-Volmer quenching constant, and [Q] is the quencher concentration (M).

Figure 4A:
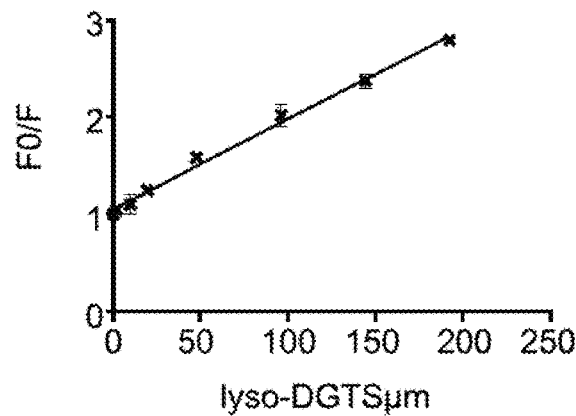
FIGS. 4A-4D show Stern-Volmer plot of the flourescence quenching of rePON1 by lyso-DGTS at 37° C. (4A) and 25° C. (4B); and double-log plot of the flourescence quenching of rePON1 by lyso-DGTS at 37° C. (4C) and 25° C. (4D). Each experiment was repeated separately three times. Results are presented as mean±SD. $R^2>0.99$ and $p<0.0001$ for all linear plots.
Figure 4B:
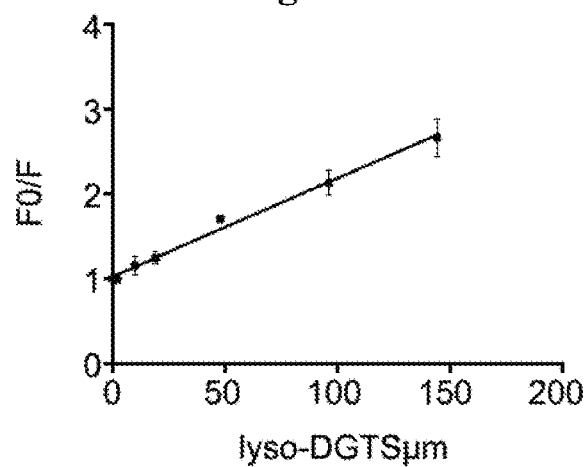

The Stern-Volmer curve (F0/F vs. [Q]) was linear at the tested concentrations of lyso-DGTS at both temperatures (with $R^2 > 0.99$ and $p < 0.0001$). The Ksv value was $(1.18 \pm 0.13) \times 10^{+4}$ $M^{-1}$ and $(0.93 \pm 0.03) \times 10^{+4}$ $M^{-1}$ for 25° C. (FIG. 4B) and 37° C. (FIG. 4A), respectively. This Ksv value indicates that the quenching is initiated via formation of a complex between the quencher and rePON1 (Atrahimovich et al., 2012).

Figure 4C:
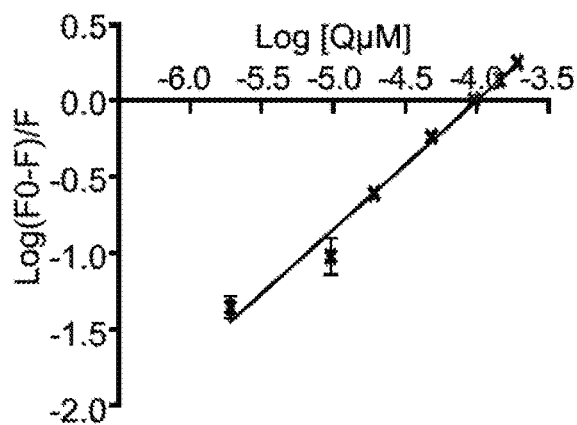
Figure 4D:
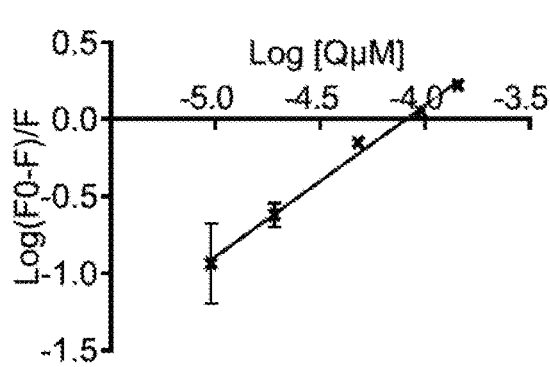

The binding constant and binding sites were calculated using (eq. 2):

$$\log\left(\frac{F0 - F}{F}\right) = \log Ka + n \log [Q] \qquad \text{Eq. 2}$$

where Ka is the binding constant, reflecting the degree of interaction between rePON1 and lyso-DGTS, and n is the number of binding sites specifying the number of lyso-DGTS molecules bound to a rePON1. The highest Ka value for the association of lyso-DGTS with rePON1 was obtained at 25° C. ($1.052 \times 10^4$ $M^{-1}$; FIG. 4D), and a lower Ka value was obtained at 37° C. ($2.377 \times 10^3$ $M^{-1}$; FIG. 4C). The values obtained for n were not affected by the temperature and were equal to ~1 (Table 4).

The thermodynamic parameters: enthalpy (ΔH), entropy (ΔS), and free energy (ΔG) were calculated to characterize the type of rePON1-lyso-DGTS interaction. Table 4 shows negative values for ΔG and for ΔH and ΔS.

TABLE 4

Binding constants (Ka), number of binding sites (n) and thermodynamic parameters for the lyso-DGTS-rePON1 interaction

| T (K) | Ka ($M^{-1}$) | ΔH (kJ/mol) | ΔG (kJ/mol) | ΔS (J/mol K) | N |
|---|---|---|---|---|---|
| 310 | $2.377 \times 10^3$ | −94.992 | −19.97 | −242.16 | 0.84 ± 0.05 |
| 298 | $1.052 \times 10^4$ | | −22.876 | | 0.98 ± 0.05 |

Example 4. Molecular Modeling Calculation of rePON1-lysoDGTS Interactions

Docking analysis of lyso-DGTS in the potential binding groove site of rePON1 was carried out to predict the location of the lyso-DGTS binding site within the complete rePON1 crystal structure and to compare the modeling prediction with the Trp.-quenching-fluorescence result. The calculated binding energy was ~−2 kcal/mol, indicating a spontaneous interaction between lyso-DGTS and rePON1. According to the docking analysis, the main dominating forces in the binding site were found to be van der waales and hydrogen bonds. These results are in accordance with the Trp. fluorescence results.

Figure 5A:
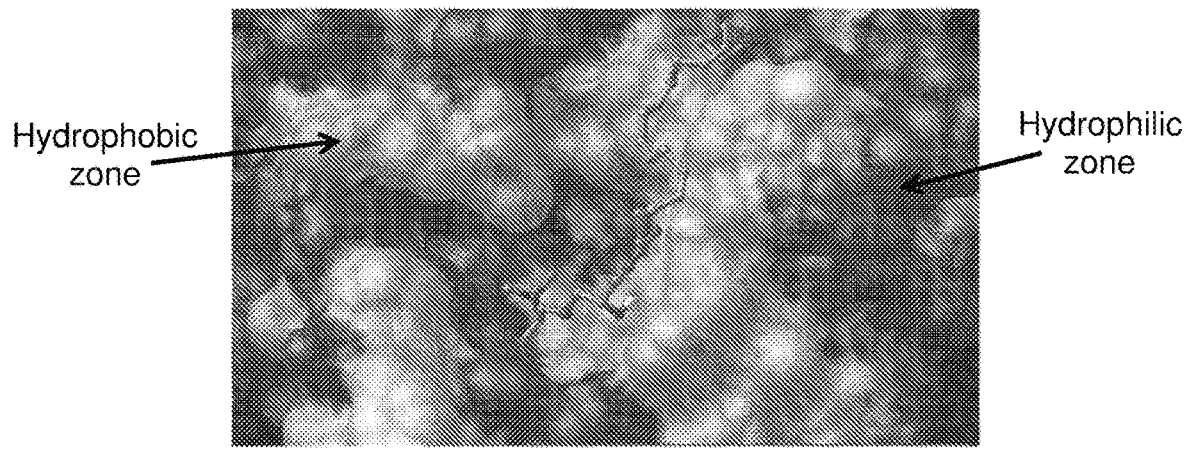
FIGS. 5A-5B show orientation of lyso-DGTS within the potential rePON1 binding site. Molecular surface of rePON1 showing hydrophilic and hydrophobic zones docked with lyso-DGTS (5A); and location of the lyso-DGTS within the rePON1 binding site showing interaction with the amino acid in the binding groove (red, oxygen; blue, nitrogen; gray, carbon) (5B).

FIG. 5A shows that the fatty acid substructure of lyso-DGTS was oriented to the hydrophobic part of the groove (blue), and the glyceryl-methylated homoserine substructure was oriented to the hydrophilic part with hydrogen bonds interactions.

Figure 5B:
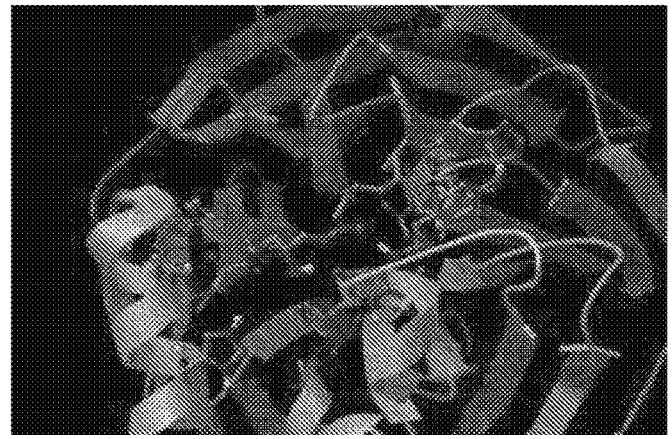

Hydrogen bonds can be observed between the carboxylic oxygen of lyso-DGTS with ser193 (distance 4.72 Å) and lys192 (distance 6.093 Å), the carbonyl group of the fatty acid of lyso-DGTS with the amine group of tyr294 (distance 1.762 Å) and the hydroxyl group of lyso-DGTS with Phe 292 (distance of 2 Å) (FIG. 5B).

Example 5. Effect of Lyso-DGTS on rePON1 Influx to Macrophage Cells

As previously shown, PON1 interacts with macrophages specifically and internalized into the cytoplasm of the cells (Efrat et al., 2008), and may thus protect the macrophages from oxidation and prevent foam cell formation. The effect of lyso-DGTS on rePON1 influx into macrophage cells is shown herein.

Figure 6A:
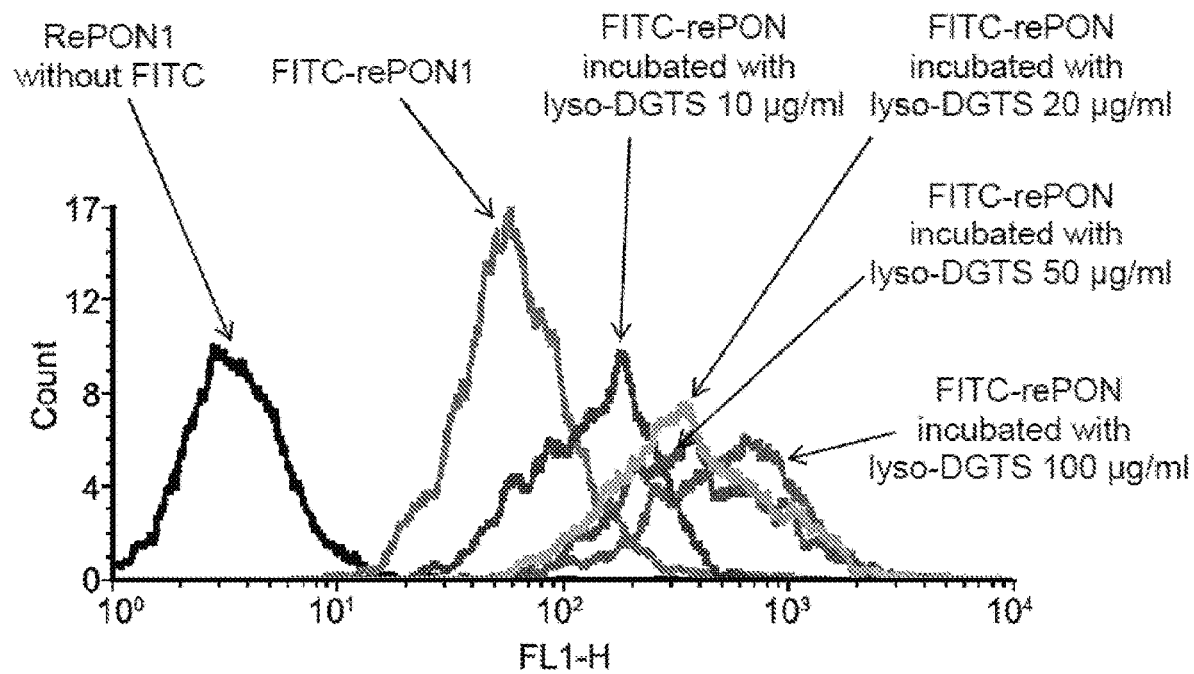
FIGS. 6A-6B show the effect of lyso-DGTS on rePON1 influx to macrophage cells. rePON1 was labeled with FITC and incubated with different concentrations of lyso-DGTS (10, 20, 50, and 100 μg/ml) for 2 h; and each solution was then added to J774A.1 cells, incubated at 37° C. for 16 h, and analyzed by FACS analysis.
Figure 6B:
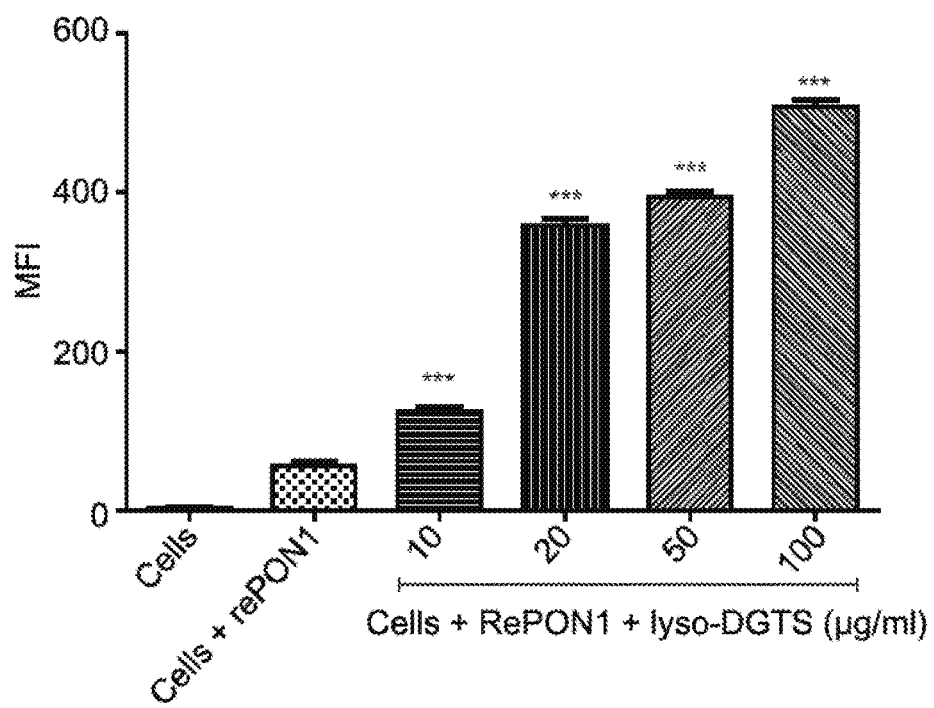

RePON1 was labeled with FITC and incubated with lyso-DGTS at different concentrations (10, 20, 50, and 100 µg/ml) for 2 h. Each solution was added to J774A.1 macrophages and incubated at 37° C. for 16 h, and then analyzed by fluorescence-activated cell sorting (FACS). FIG. 6A shows that lyso-DGTS significantly increased rePON1 internalization into macrophages in a dose dependent manner. The MFI increased from 61.62 for rePON1-FITS alone to 131.02, 368.61, 386.46, and 517.45 for rePON1 incubated with lyso-DGTS at 10, 20, 50, and 100 µg/ml, respectively (FIG. 6B).

Example 6. The Effect of Lyso-DGTS-rePON1 Interaction on Ox-LDL-Induced Foam Cell Formation in J774A.1 Macrophages Macrophages uptake of ox-LDL, forming foam cell, is the hallmark of atherogenesis. The ability of lyso-DGTS or rePON1 incubated with lyso-DGTS to attenuate foam cell formation was examined. J774A.1 macrophages were incubated with rePON1 (50 µg/ml), rePON1 pre-incubated with lyso-DGTS (50 and 100 µg/ml) or lyso-DGTS (50 µg/ml) alone, and were then washed and incubated with ox-LDL (25 µg/ml) for 24 h.

Figure 7A:
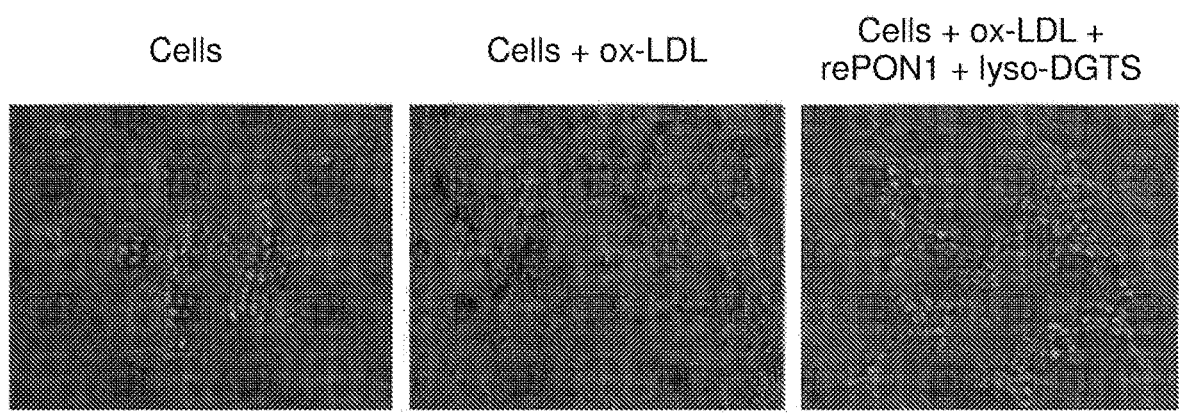
FIGS. 7A-7B show the effect of lyso-DGTS-rePON1 interaction on ox-LDL-induced foam cell formation in J774A.1 macrophage cells. RePON1 (50 μg/ml), rePON1 with lyso-DGTS (50 or 100 μg/ml) and lyso-DGTS (50 μg/ml) were incubated for 2 h, added to cells and incubated for 24 h, and the cells were then treated with ox-LDL (25 μg/ml) for another 24 h. Oil red O staining was performed to analyze foam cell formation, and representative images are shown in FIG. 7A. Intensity of lipid accumulation into cells was quantified by alcohol extraction, and absorbance was measured at 514 nm as shown in FIG. 7B. #$p<0.05$ related to control (untreated cells), *$p<0.05$, and **$p<0.01$ related to cells treated with ox-LDL alone. Statistics was analyzed using one-way ANOVA and Graphpad prism 5 software. Data are the means±SD from 3 experiments.
Figure 7B:
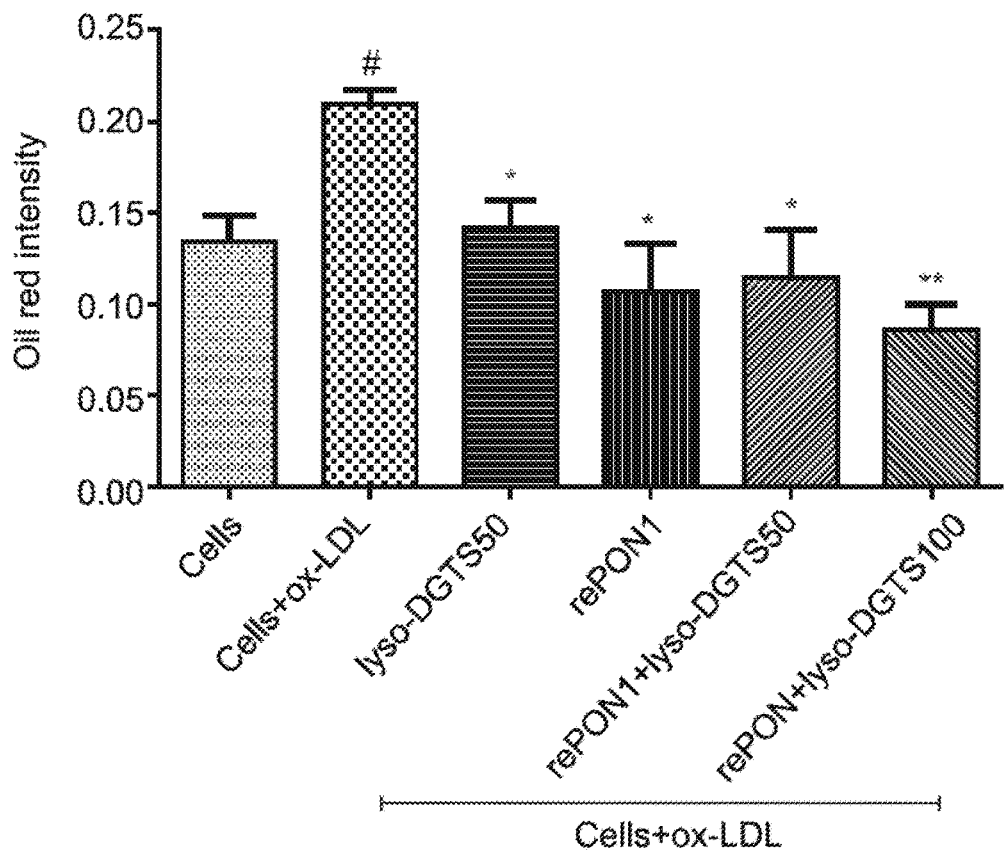

Incubation of the cells with ox-LDL resulted in lipid deposition in macrophages and foam cell formation (FIG. 7A). The quantitative analysis of oil red staining intensity showed that pre-incubation of the macrophages with lyso-DGTS alone significantly reduced the oil red staining intensity by 32%. While pre-incubation of the cells with rePON1 and rePON1 incubated with lyso-DGTS at 50 and 100 µg/ml significantly reduced the oil red intensity by 49%, 45% and 60% respectively (FIG. 7B). The results confirm the ability of lyso-DGTS to inhibit ox-LDL-induced foam cell formation. Also, rePON1 inhibited ox-LDL-induced foam cell formation while incubation of the enzyme with 100 µg/ml lyso-DGTS enhanced its ability to inhibit foam cell formation by ~10% (not significant).

Figure 8:
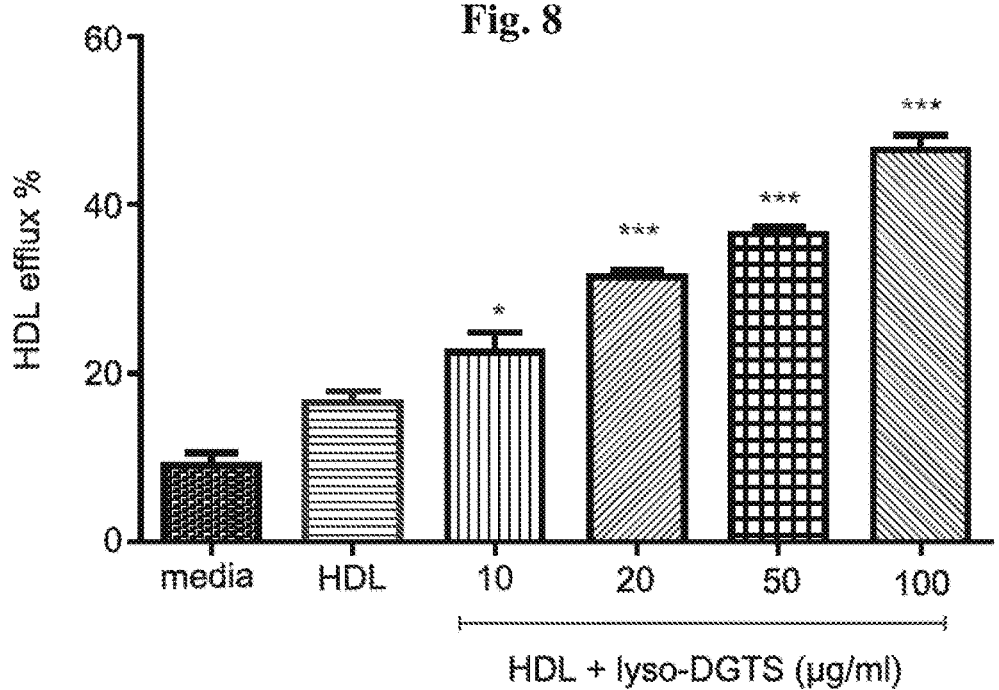
FIG. 8 shows the effect of lyso-DGTS on HDL-mediated cholesterol efflux from macrophage cells. J774A.1 cells were incubated for 16 h with 50 μl fluorescently-labeled cholesterol and 50 μl equilibration buffer. The cells were washed and further incubated for 4 h with RPMI buffer (media), HDL (25 μg protein) incubated with 2 μl DMSO, or HDL (25 μg protein) incubated with 2 μl lyso-DGTS dissolved in DMSO at a final concentration of 10, 20, 50, and 100 μg/ml for 4 h. Fluorescence was measured in the media and the cells at excitation/emission 482/515 nm. The cholesterol efflux was expressed as % efflux elicited by cells. Each experiment was repeated separately at least three times. *$p<0.05$, ***$p<0.0001$ related to the control (HDL incubated with DMSO). n=3. Statistics were analyzed using one-way ANOVA and Graphpad prism 5 software.

Example 7. The Effect of Lyso-DGTS on HDL-Mediated Cholesterol Efflux from Macrophage Cells HDL removes cholesterol from cells, including macrophages. HDL particles were incubated with lyso-DGTS at different concentrations. The HDL ability to efflux cholesterol from J774A.1 macrophages was measured using flouromtric assay (cell-based cholesterol efflux flouromtric assay kit, supplied by Biovision) and expressed as % of cholesterol efflux. Lyso-DGTS significantly increased the ability of HDL to take out cholesterol from macrophages in a dose dependent manner. The cholesterol removal enhanced from 16.5% (without lyso-DGTS) to 22.5%, 31.5%, 36.5%, and 46.5% after incubation with lyso-DGTS at 10, 20, 50, and 100 µg/ml, respectively (FIG. 8).

Example 8. The Effect of Lyso-DGTS on APOA1-Mediated Cholesterol Efflux from Macrophage Cells Apolipoprotein A1 (APOA1) is the major structural and functional HDL protein which accounts for approximately 70% of total HDL protein. It has been repeatedly demonstrated that APOA1 is a particularly efficient acceptor of cholesterol released from cells. The effect of lyso-DGTS on APOA1 mediated cholesterol efflux from macrophage cells was examined.

Figure 9:
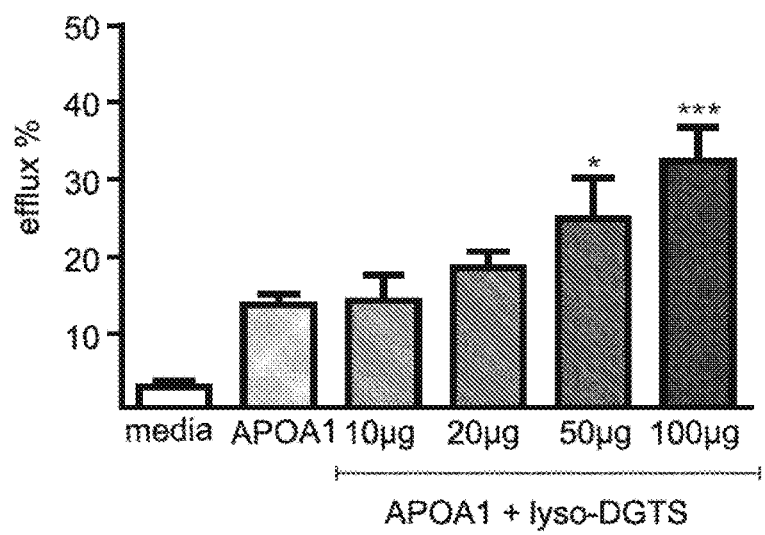
FIG. 9 shows the effect of lyso-DGTS on APOA1-mediated cholesterol efflux from macrophage cells. J774A.1 cells were incubated for 4 h with RPMI buffer (media), APOA1 (10 μg) preincubated with DMSO or with lyso-DGTS (at final concentration of 10, 20, 50, and 100 μg/ml) for 2 h. Fluorescence was measured in media and cells at excitation/emission 482/515 nm. The cholesterol efflux was expressed as % efflux elicited by cells. Each experiment was repeated separately at least three times. *$p<0.05$, ***$p<0.0001$ relative to the control (APOA1 incubated with DMSO; n=3). Statistical analysis by one-way ANOVA and Graphpad prism 5 software.

APOA1 was incubated with lyso-DGTS at different concentrations (0, 10, 20, 50, and 100 µg/ml), and its ability to remove cholesterol from J774A.1 macrophages was measured by fluorometric assay (cell-based Cholesterol Efflux Fluorometric Assay Kit) and expressed as % of cholesterol efflux. FIG. 9 shows that lyso-DGTS significantly enhanced the APOA1 cholesterol efflux from macrophage cells in a dose dependent manner, starting at APOA1+50 µg/ml lyso-DGTS (~25%; p<0.05) up to max APOA1 efflux at 100 µg/ml lyso-DGTS (~35%; p<0.0001).

Figure 10A:
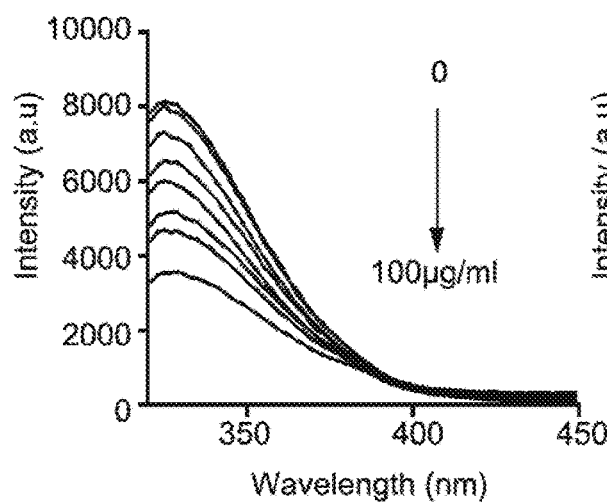
FIGS. 10A-10B show tryptophan fluorescence spectra of HDL (0.03 mg/ml) incubated with/without lyso-DGTS at various concentrations (1, 5, 10, 25, 50, 75, and 100 μg/ml) in black 96-well plates for 4 h at 37° C. (10A) or 25° C. (10B). The fluorescence was measured at excitation/emission 290/320-340 nm. The ability of lyso-DGTS to elevate HDL activity correlates with its binding affinity to HDL. Each experiment repeated separately at least three times.
Figure 10B:
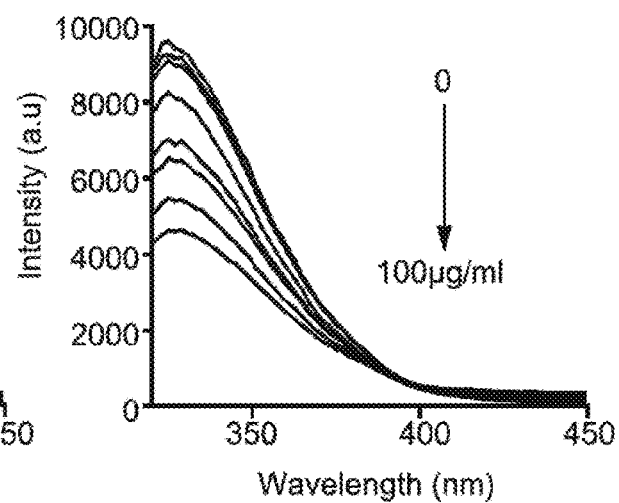

Example 9. Investigation of HDL-Lyso-DGTS and APOA1-Lyso-DGTS Interactions Using Trp-Fluorescence-Quenching Method In order to test whether the protective effect of lyso-DGTS on HDL occurs via specific interaction between lyso-DGTS and the lipoprotein, the HDL-lyso-DGTS interaction was investigated by the Trp-fluorescence-quenching method. FIG. 10 shows the emission spectra of HDL in the presence of various concentrations of lyso-DGTS at 37° C. (FIG. 10A) and 25° C. (FIG. 10B) in the 300-450 nm range with an excitation wavelength of 290 nm. Lyso-DGTS quenched HDL fluorescence in a dose-dependent manner at both temperatures.

Figure 11A:
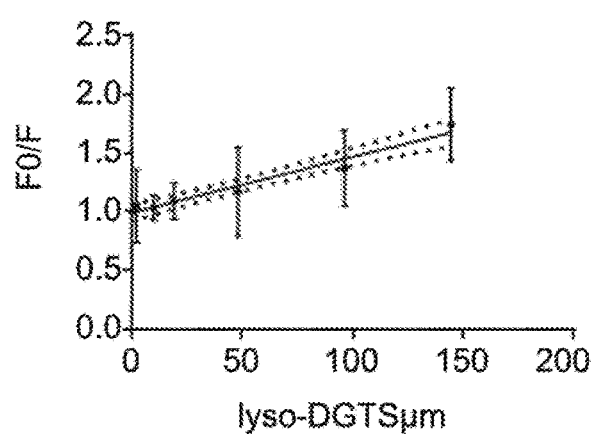
FIG. 11A-11D show Stern-Volmer plot of the fluorescence quenching of HDL by lyso-DGTS at 37° C. (11A) and 25° C. (11B); and double-log plot of the fluorescence quenching of HDL by lyso-DGTS at 37° C. (11C) and 25° C. (11D). Each experiment was repeated separately at least three times. Results are presented as mean±SD. $R^2>0.99$ and $p<0.0001$ for all linear plots.
Figure 11B:
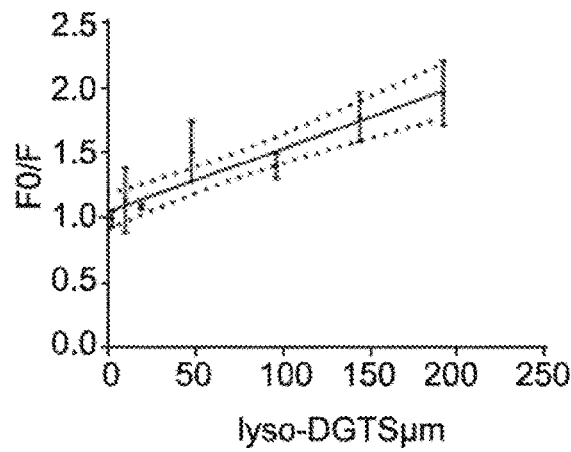

Quenching pathways can be described by the Stern-Volmer equation (eq. 1 above). The Stern-Volmer curve was linear at the tested concentration of lyso-DGTS at both temperatures (with R>0.99 and p<0.0001). The Ksv values were $(5.59\pm0.42)\times10^3$ $M^{-1}$ at 37° C. (FIG. 11A) and $(4.83\pm0.59)\times10^3$ $M^{-1}$ at 25° C. (FIG. 11A), indicating that the quenching is initiated via formation of a complex between the quencher and HDL.

Figure 11C:
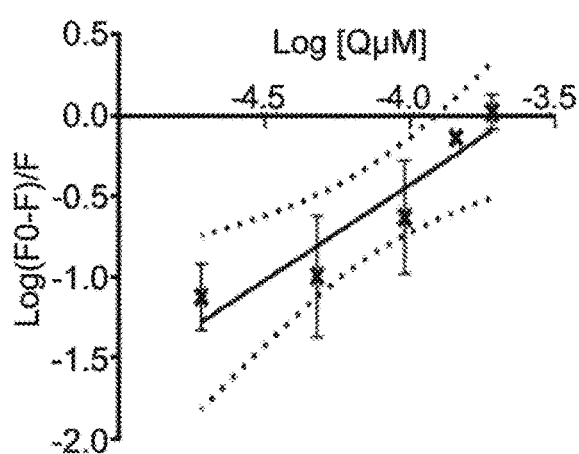
Figure 11D:
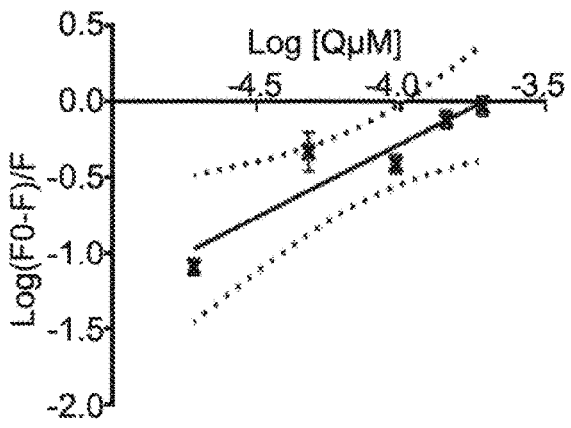

The binding constant and binding sites were calculated as shown for rePON1, using eq. 2 above. The highest Ka value for the association of lyso-DGTS with HDL at 37° C. was $2.165\times10^4$ $M^{-1}$ (FIG. 11C), decreasing to $3.78\times10^3$ $M^{-1}$ at 25° C. (FIG. 11D). The values obtained for n were not affected by temperature and were equal to 1 (Table 5). The thermodynamic parameters: enthalpy ($\Delta H$), entropy ($\Delta S$), and free energy ($\Delta G$) were calculated to characterize the HDL-lyso-DGTS interaction type. Table 5 shows negative values for $\Delta G$, and positive values for $\Delta H$ and $\Delta S$, indicating a spontaneous interaction supported by hydrophobic forces.

TABLE 5

Binding constants (Ka), number of binding sites (n) and thermodynamic parameters for the lyso-DGTS-HDL interaction

| T (K) | Ka (M$^{-1}$) | ΔH (kJ/mol) | ΔG (kJ/mol) | ΔS (J/mol K) | N |
|---|---|---|---|---|---|
| 310 | 2.165 × 10$^4$ | 26.6 | −6.127 | 105.59 | 1.19 ± 0.05 |
| 298 | 3.78 × 10$^3$ |  | −4.86 |  | 0.96 ± 0.05 |

The Trp-fluorescence-quenching method was further used to examine the interaction between lyso-DGTS and APOA1, the major protein component of HDL. Ka and thermodynamic parameters were also calculated (Table 6). The highest Ka value for the association of lyso-DGTS with APOA1 at 37° C. was 2.28×10$^4$ M$^{-1}$, decreasing to 2.37×10$^3$ M$^{-1}$ at 25° C. The values obtained for n were not affected by temperature and were equal to=1 (Table 6).

The thermodynamic parameters: enthalpy (ΔH), entropy (ΔS), and free energy (ΔG) were calculated to characterize the APOA1-lyso-DGTS interaction type. Table 6 shows negative values for ΔG, and positive values for ΔH and ΔS, indicating a spontaneous interaction supported by hydrophobic forces. The parameters obtained for the lyso-DGTS-APOA1 interaction were similar to those obtained for lyso-DGTS-HDL interaction, indicating that lyso-DGTS mainly interacts with APOA1 in the HDL particle.

TABLE 6

Binding constants (Ka), number of binding sites (n) and thermodynamic parameters for the lyso-DGTS-APOA1 interaction

| T (K) | Ka (M$^{-1}$) | ΔH (kJ/mol) | ΔG (kJ/mol) | ΔS (J/mol K) | N |
|---|---|---|---|---|---|
| 310 | 2.28 × 10$^4$ | 34.49 | −6.125 | 131.126 | 1.23 ± 0.05 |
| 298 | 2.37 × 10$^3$ |  | −4.58 |  | 1.01 ± 0.05 |

Example 10. The Effect of Lyso-DGTS on HDL Surface Polarity

Figure 12:
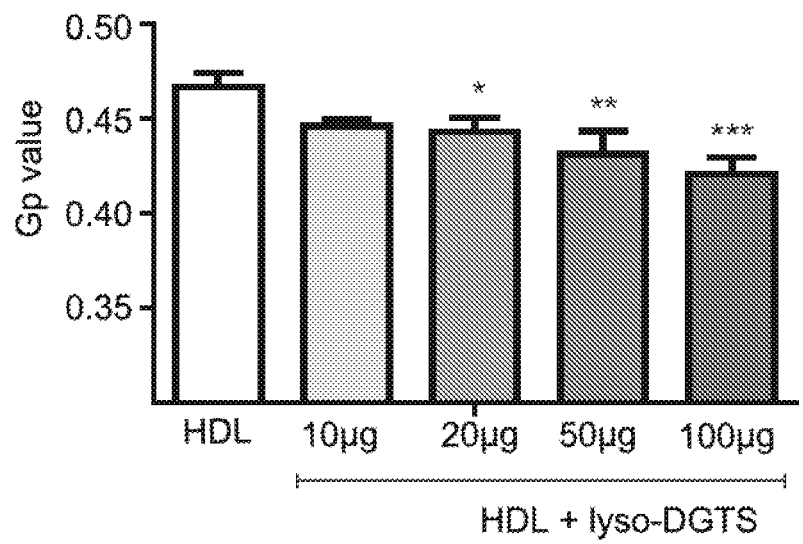
FIG. 12 shows General Polarization (Gp) values of Laurdan incorporated in HDL (100 µg/ml) incubated with lyso-DGTS at various concentrations (0, 10, 20, 50, and 100 µg/ml). The fluorescence emission spectra of Laurdan were obtained using at excitation/emission 340/400-520 nm. The value of Gp of Laurdan was calculated using the formula: $Gp=(I435-I490)/(I435+I490)$. Each experiment was repeated separately at least three times. *$p<0.05$, ***$p<0.0001$ related to the control (HDL without lyso-DGTS). Statistics were analyzed using T-test Graphpad prism 5 software.

HDL particles are plurimolecular, quasi-spherical or discoid, pseudomicellar complexes predominantly composed of polar lipids solubilized by apolipoproteins. In order to determine a possible interaction between lyso-DGTS and the HDL lipid core, the Laurdan General Polarization (Gp) assay was used. Gp values of Laurdan incorporated with HDL incubated with graded doses of lyso-DGTS were measured, and as shown, lyso-DGTS significantly decreased the HDL Gp values at a dose dependent manner at 20, 50, and 100 μg/ml, indicating an increase of the HDL lipid core polarity when incubated with lyso-DGTS (FIG. 12). These results show that lyso-DGTS interacts with the HDL proteomics and lipidomics. This interaction may cause a change in its physical state and lipid core polarity and thus affect its functionality.

Example 11. The Effect of Lyso-DGTS on HDL Ability to Induce Endothelial Nitric Oxide (NO) Release NO is a soluble gas continuously synthesized from the amino acid L-arginine in endothelial cells by the constitutive calcium-calmodulin-dependent enzyme nitric oxide synthase (NOS). This substance has a wide range of biological properties that maintain vascular homeostasis, including modulation of vascular dilator tone, regulation of local cell growth, and protection of the vessel from injurious consequences of platelets and cells circulating in blood, playing in this way a crucial role in the normal endothelial function. The effect of lyso-DGTS on the ability of HDL to induce endothelial NO release was examined and the results were compared to Sphingosine 1-Phosphate (S1P), an important lipid component identified in HDLs that may account for NO-mediated vasodilatory effects of HDLs.

Figure 13:
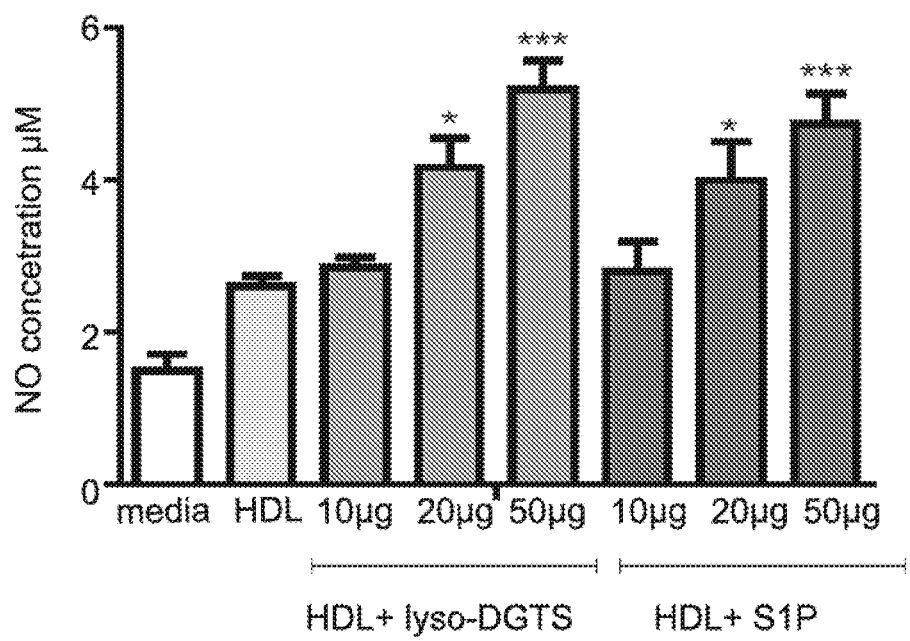
FIG. 13 shows human umbilical vein endothelial cell (HUVEC) nitric oxide (NO) production detected by the DAN assay after reducing culture media with nitrate reductase. HUVECs were stimulated for 2 h with HDL (50 µg/ml) preincubated with DMSO, lyso-DGTS and S1P at final concentrations of 10, 20, and 50 µg/ml for 3 h. Media were then collected and treated with nitrate reductase followed by analysis using the DAN assay. Data are expressed as NO concentration (µM) released by the cells. Each experiment was repeated separately at least three times. *$p<0.05$, ***$p<0.0001$ related to the control (HDL without lyso-DGTS or S1P). Statistics were analyzed using one-way annova Graphpad prism 5 software.

Human umbilical vein endothelial cells (HUVECs) were incubated for 2 hours with HDL preincubated with different concentration of lyso-DGTS or S1P for 3 hours, and NO production determined using 2,3-diaminonapthalene (DAN) assay. Similar to S1P, lyso-DGTS significantly increased the HDL ability to induce endothelial NO release at a dose dependent manner (FIG. 13).

Example 12. The Effect of Lyso-DGTS on Serum PON1 Lactonase Activity on Balb/c Mice Fed with High Fat Diet (HFD)

Figure 14:
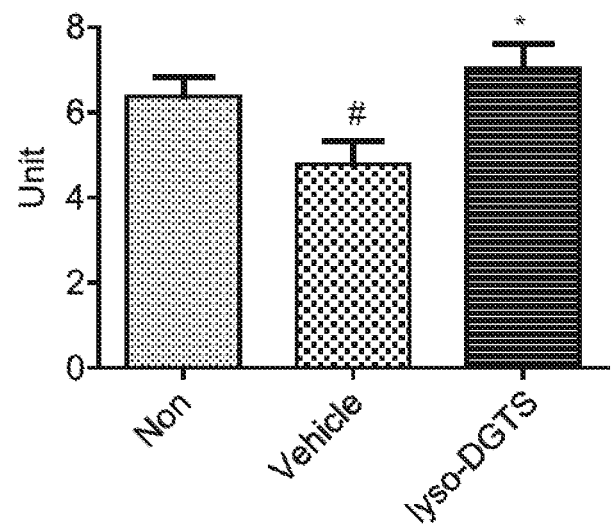
FIG. 14 shows the effect of lyso-DGTS on serum PON1 lactonase activity of Balb/c mice. Balb/c mice were fed with either normal rodent diet (the "non" group; n=11) or high-fat diet (HFD), and received treatment administered via subcutaneously implanted osmotic mini-pumps: 1) vehicle group injected with DDW+2% Tween 80 (n=9); 2) lyso-DGTS group injected with lyso-DGTS (1.43 mg/ml in DDW+2% Tween 80; n=11). At the end of the protocol, serum was produced and diluted by 20 with PBS, and PON1 lactonase activity was measured using dihydrocumarine assay. Statistics was analyzed using one-way ANOVA and Graphpad prism 5 software. #$p<0.05$ related to the "non" group and *$p<0.05$ related to the vehicle group.

The effect of lyso-DGTS on lactonase PON1 activity was examined using Balb/c mice fed with HFD. Three groups of Balb/c mice were used: 1) the "non" group n=1 mice which was fed with normal rodent diet for 12 weeks; 2) the "vehicle" group n=9 mice which was fed with HFD for 8 weeks and then continued with the same diet for another 4 weeks with the injection of DDW+2% Tween via osmotic mini-pumps implanted subcutaneously; and 3) the lyso-DGTS group n=1 mice which was fed similar to the vehicle group and injected with lyso-DGTS at 1.43 mg/ml in DDW+2% Tween 80 (FIG. 14). At the end of the protocol, blood was withdrawn and clinical parameters and lactonase PON1 activity were measured. The body weight and cholesterol levels in the blood of the mice fed with HFD were significantly higher than those in mice fed with normal diet. HFD increased blood glucose level from 6.3±1.6 μM in the "non" group to 7.15±0.74 in the "vehicle" group (not statistically significant), while injecting the mice with lyso-DGTS significantly decreased blood glucose levels to 5.99±1.4 μM (Table 7). Lactonase PON1 activity of the mice serum was measured using dehydrocumarine assay. HFD significantly decreased mice serum lactonase PON1 activity (decrease of ~2 units) and injecting the mice with lyso-DGTS significantly increased their serum lactonase PON1 activity (increase of ~2.3 units).

TABLE 7

Clinical parameters of the in-vivo experiment

|  | Non 12 | Vehicle 12 | Lyso-DGTS 12 |
|---|---|---|---|
| n |  |  |  |
| BW (end of protocol) | 27.4 ± 2.1 | 30.4 ± 1.9$^a$ | 29.8 ± 2.4$^a$ |
| Delta BW* | 4.1 ± 2.0 | 6.5 ± 2.2$^{a1}$ | 5.7 ± 2.18 |
| Glucose (μM) | 6.3 ± 1.6 | 7.15 ± 0.74 | 5.99 ± 1.4$^b$ |
| Triglycerides (μM) | 0.77 ± 0.40 | 0.98 ± 0.31 | 0.84 ± 0.26 |
| Cholesterol (μM) | 3.66 ± 0.39 | 4.25 ± 0.62$^a$ | 4.03 ± 0.40 |
| HDL (μM) | 3.57 ± 0.52 | 4.39 ± 1.05 | 4.37 ± 0.42$^{a1}$ |

*The change in body weight from baseline (at the beginning of the experiment, time zero);
$^a$p < 0.05 related to non group;
$^{a1}$p < 0.01 related to non group;
$^b$p < 0.05 related to vehicle group.

Figure 15:
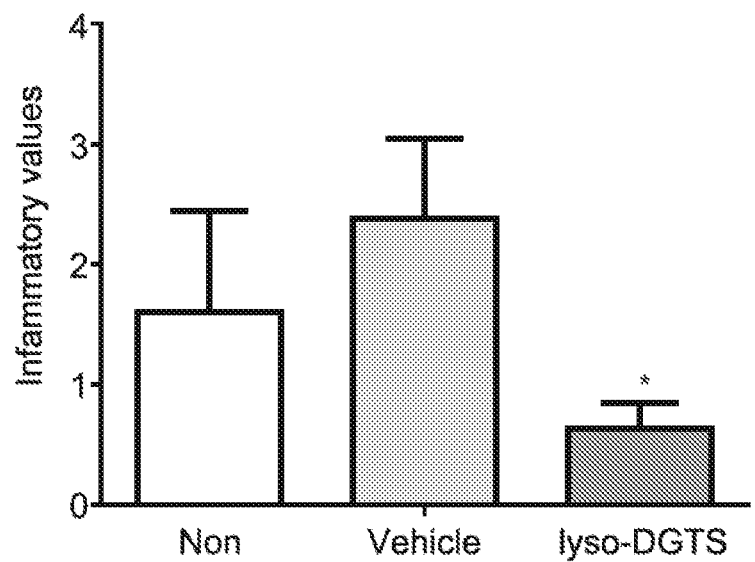
FIG. 15 shows the effect of lyso-DGTS on the pro-inflammatory/anti-inflammatory properties of HDL isolated from Balb/c mice. Balb/c mice fed with normal rodent diet (the "non" group; n=11) or HFD received treatment administered via subcutaneously implanted osmotic mini-pumps: 1) vehicle group injected with DDW+2% Tween 80 (n=9); 2) lyso-DGTS group injected with lyso-DGTS (1.43 mg/ml in DDW+2% Tween 80; n=1). At the end of the protocol, serum was obtained, HDL was isolated, and its pro-inflammatory/anti-inflammatory properties were determined using cell free assay (CFA). Fluorescence in the absence of HDL was normalized to 1.0. Values>1.0, after addition of the tested HDL, indicated pro-inflammatory activity; and values<1.0 indicated anti-inflammatory activity. (*$p<0.05$).

Example 13. The Effect of Lyso-DGTS on the Anti-Inflammatory Properties of HDL in High Fat Diet (HFD) Fed Balb/c Mice In order to examine the effect of lyso-DGTS on HDL-anti-inflammatory effects in-vivo, 3.5 μl lyso-DGTS a day were administered for 28 days, via a subcutaneously implanted osmotic mini-pump, to HFD fed mice. As described in Example 12, the mice were divided into three groups: 1) mice fed with regular diet for 12 weeks (the "non" group; n=1); 2) mice fed with HFD for 12 weeks and injected with lyso-DGTS (1.43 mg/ml in DDW+2% Tween) from week 9 (the lyso-DGTS group; n=1); and 3) mice fed with HFD for 12 weeks and injected with DDW+2% Tween (the vehicle group; n=9). As found, HDL isolated from the lyso-DGTS group showed a significantly lower inflammatory value (inflammatory value<1; p<0.05) as compared to HDL isolated from the vehicle group and from the non group which showed pro-inflammatory properties (inflammatory values>1; p<0.05) (FIG. 15), indicating that lyso-DGTS enhances HDL anti-inflammatory properties in HFD fed mice.

Example 14. Preparation of Lyso-DGTS Derivatives

In this study, lyso-DGTS derivatives are synthesized and tested for their activity.

In certain derivatives, the EPA residue of lyso-DGTS is replaced with a residue of a different fatty acid. Since EPA is a polyunsaturated fatty acid that might be easily oxidized, the alternative fatty acid used are either saturated fatty acids, e.g., palmitic acid, or an unsaturated fatty acid having one, two or three double bonds only, e.g., oleic acid, linoleic acid, and linolenic acid, respectively. The synthesis of such lyso-DGTS derivatives is schematically depicted in Scheme 1.

In other derivatives, the fatty acid residue of lyso-DGTS is linked to the glyceryl via an amide bond rather than ester bond. Since amide bond is more stable than ester bond, such compounds are expected to be more stable than lyso-DGTS and might thus be administered orally. Yet, it should be noted that in such derivatives, the glyceryl nuclei is replaced with a ceramide-like nuclei having an amino group replacing a terminal hydroxyl group rather than the hydroxyl group at position 2, as in the case of ceramide. The synthesis of such lyso-DGTS derivatives is schematically depicted in Scheme 2.

In further derivatives, a fatty acid residue is linked directly, via either an ester or an amide bond to a terminal carbon atom of the side chain of an alpha amino acid having a quaternary ammonium. The synthesis of such lyso-DGTS derivatives is schematically depicted in Schemes 3 and 4.

Scheme 1. Synthesis of compounds o the formula Ia

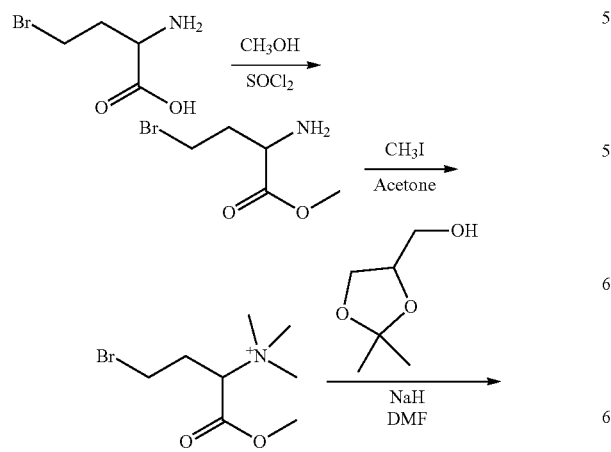

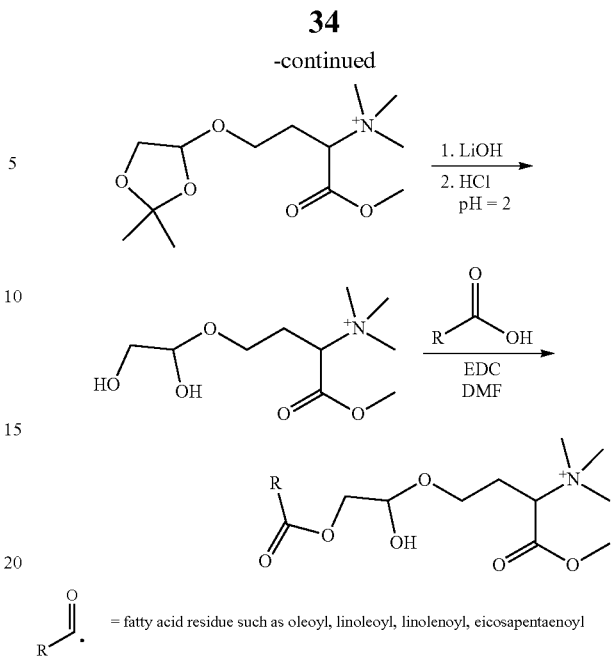

Scheme 2. Synthesis of compounds o the formula Ib

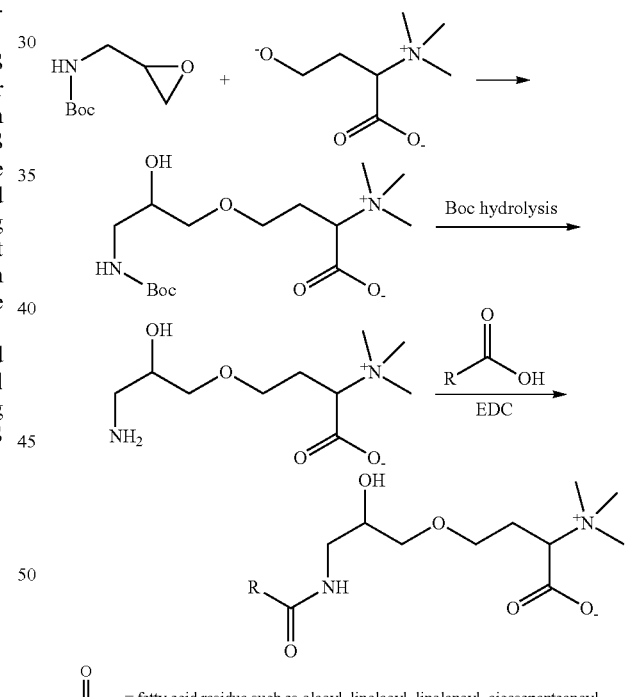

Scheme 3. Synthesis of compounds o the formula Ic

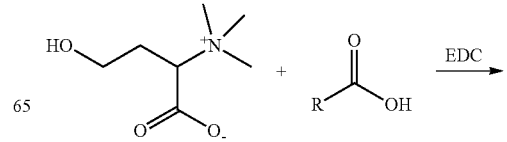

-continued

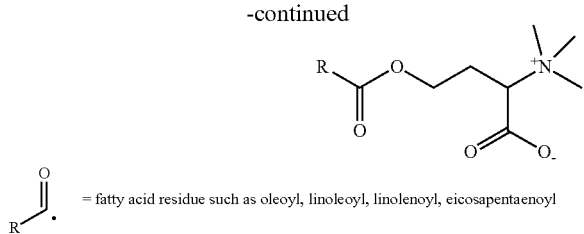

= fatty acid residue such as oleoyl, linoleoyl, linolenoyl, eicosapentaenoyl

Scheme 4. Synthesis of compounds o the formula Id

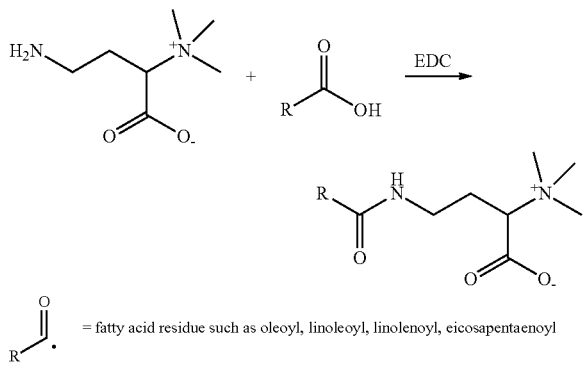

= fatty acid residue such as oleoyl, linoleoyl, linolenoyl, eicosapentaenoyl

REFERENCES

Atrahimovich, D.; Vaya, J.; Khatib, S., The effects and mechanism of flavonoid-rePON1 interactions. Structure-activity relationship study. *Bioorganic & medicinal chemistry* 2013, 21, 3348-3355

Atrahimovich, D.; Vaya, J.; Tavori, H.; Khatib, S., Glabridin protects paraoxonase 1 from linoleic acid hydroperoxide inhibition via specific interaction: a fluorescence-quenching study. *Journal of agricultural and food chemistry* 2012, 60, 3679-3685

Barter, P. J.; Puranik, R.; Rye, K. A., New insights into the role of HDL as an anti-inflammatory agent in the prevention of cardiovascular disease. *Current cardiology reports* 2007, 9, 493-498

Ben-David, M.; Elias, M.; Filippi, J. J.; Dunach, E.; Silman, I.; Sussman, J. L.; Tawfik, D. S., Catalytic versatility and backups in enzyme active sites: the case of serum paraoxonase 1. *Journal of molecular biology* 2012, 418, 181-196

Cohen, E.; Aviram, M.; Khatib, S.; Artoul, F.; Rabin, A.; Mannheim, D.; Karmeli, R.; Salamon, T.; Vaya, J., Human carotid plaque phosphatidylcholine specifically interacts with paraoxonase 1, increases its activity, and enhances its uptake by macrophage at the expense of its binding to HDL. *Free radical biology & medicine* 2014, 76, 14-24

Craciun, E. C.; Leucuta, D. C.; Rusu, R. L.; David, B. A.; Cret, V.; Dronca, E., Paraoxonase-1 activities in children and adolescents with type 1 diabetes mellitus. *Acta biochimica Polonica* 2016, 63, 511-515

Efrat, M.; Aviram, M., Macrophage paraoxonase 1 (PON1) binding sites. *Biochemical and biophysical research communications* 2008, 376, 105-110

Fuhrman, B.; Volkova, N.; Aviram, M., Postprandial serum triacylglycerols and oxidative stress in mice after consumption of fish oil, soy oil or olive oil: possible role for paraoxonase-1 triacylglycerol lipase-like activity. *Nutrition* 2006, 22, 922-930

Gu, X.; Huang, Y.; Levison, B. S.; Gerstenecker, G.; DiDonato, A. J.; Hazen, L. B.; Lee, J.; Gogonea, V.; DiDonato, J. A.; Hazen, S. L., Identification of Critical Paraoxonase 1 Residues Involved in High Density Lipoprotein Interaction. *The Journal of biological chemistry* 2016, 291, 1890-1904

Gugliucci, A.; Caccavello, R.; Nassar, H.; Abu Ahmad, W.; Sinnreich, R.; Kark, J. D., Low protective PON1 lactonase activity in an Arab population with high rates of coronary heart disease and diabetes. *Clinica chimica acta; international journal of clinical chemistry* 2015, 445, 41-47

Gupta, N.; Binukumar, B. K.; Singh, S.; Sunkaria, A.; Kandimalla, R.; Bhansali, A.; Gill, K. D., Serum paraoxonase-1 (PON1) activities (PONase/AREase) and polymorphisms in patients with type 2 diabetes mellitus in a North-West Indian population. *Gene* 2011, 487, 88-95

Gur, M.; Cayli, M.; Ucar, H.; Elbasan, Z.; Sahin, D. Y.; Gozukara, M. Y.; Selek, S.; Koyunsever, N. Y.; Seker, T.; Turkoglu, C.; Kaypakli, O.; Aksoy, N., Paraoxonase (PON1) activity in patients with subclinical thoracic aortic atherosclerosis. *The international journal of cardiovascular imaging* 2014, 30, 889-895

Hafiane, A.; Genest, J., High density lipoproteins: Measurement techniques and potential biomarkers of cardiovascular risk. *BBA clinical* 2015, 3, 175-188

Hatzihidiroglou, A.; Makedou, K.; Savopoulos, C., Prevalence of paraoxonase-1 polymorphisms in diabetes mellitus type 2 Greek patients. *Hippokratia* 2016, 20, 176

Hernaez, A.; Castaner, O.; Elosua, R.; Pinto, X.; Estruch, R.; Salas-Salvado, J.; Corella, D.; Aros, F.; Serra-Majem, L.; Fiol, M.; Ortega-Calvo, M.; Ros, E.; Martinez-Gonzalez, M. A.; de la Torre, R.; Lopez-Sabater, M. C.; Fito, M., Mediterranean Diet Improves High-Density Lipoprotein Function in High-Cardiovascular-Risk Individuals: A Randomized Controlled Trial. *Circulation* 2017, 135, 633-643

Jamuna Rani, A.; Mythili, S. V.; Nagarajan, S., Study on paraoxonase 1 in type 2 diabetes mellitus. *Indian journal of physiology and pharmacology* 2014, 58, 13-16

Jian, B.; de la Llera-Moya, M.; Ji, Y.; Wang, N.; Phillips, M. C.; Swaney, J. B.; Tall, A. R.; Rothblat, G. H., Scavenger receptor class B type I as a mediator of cellular cholesterol efflux to lipoproteins and phospholipid acceptors. *The Journal of biological chemistry* 1998, 273, 5599-5606

Juretic, D.; Motejlkova, A.; Kunovic, B.; Rekic, B.; Flegar-Mestric, Z.; Vujic, L.; Mesic, R.; Lukac-Bajalo, J.; Simeon-Rudolf, V., Paraoxonase/arylesterase in serum of patients with type II diabetes mellitus. *Acta pharmaceutica* 2006, 56, 59-68

Khera, A. V.; Cuchel, M.; de la Llera-Moya, M.; Rodrigues, A.; Burke, M. F.; Jafri, K.; French, B. C.; Phillips, J. A.; Mucksavage, M. L.; Wilensky, R. L.; Mohler, E. R.; Rothblat, G. H.; Rader, D. J., Cholesterol efflux capacity, high-density lipoprotein function, and atherosclerosis. *The New England journal of medicine* 2011, 364, 127-135

Levkau, B., HDL-S1P: cardiovascular functions, disease-associated alterations, and therapeutic applications. *Frontiers in pharmacology* 2015, 6, 243

Lou-Bonafonte, J. M.; Gabas-Rivera, C.; Navarro, M. A.; Osada, J., The Search for Dietary Supplements to Elevate or Activate Circulating Paraoxonases. *International journal of molecular sciences* 2017, 18, 416

Mackness, B.; Durrington, P.; McElduff, P.; Yarnell, J.; Azam, N.; Watt, M.; Mackness, M., Low paraoxonase activity predicts coronary events in the Caerphilly Prospective Study. *Circulation* 2003, 107, 2775-2779

Mackness, M.; Mackness, B., Human paraoxonase-1 (PON1): Gene structure and expression, promiscuous activities and multiple physiological roles. *Gene* 2015, 567, 12-21

Miller, N. E.; La Ville, A.; Crook, D., Direct evidence that reverse cholesterol transport is mediated by high-density lipoprotein in rabbit. *Nature* 1985, 314, 109-111 Noack, B.; Aslanhan, Z.; Boue, J.; Petig, C.; Teige, M.; Schaper, F.; Hoffmann, T.; Hannig, C., Potential association of paraoxonase-1, type 2 diabetes mellitus, and periodontitis. *Journal of periodontology* 2013, 84, 614-623

Nofer, J. R.; Assmann, G., Atheroprotective effects of high-density lipoprotein-associated lysosphingolipids. *Trends in cardiovascular medicine* 2005, 15, 265-271

Oram, J., HDL apolipoprotein and ABCA1. Partners in the removal of excess cellular cholesterol. *Arteriosclerosis, thrombosis, and vascular biology* 2003, 23, 720-727

Pirillo, A.; Norata, G. D.; Catapano, A. L., Treating high density lipoprotein cholesterol (HDL-C): quantity versus quality. *Current pharmaceutical design* 2013, 19, 3841-3857

Poti, F.; Simoni, M.; Nofer, J. R., Atheroprotective role of high-density lipoprotein (HDL)-associated sphingosine-1-phosphate (S1P). *Cardiovascular research* 2014, 103, 395-404

Rosenblat, M.; Gaidukov, L.; Khersonsky, O.; Vaya, J.; Oren, R.; Tawfik, D. S.; Aviram, M., The catalytic histidine dyad of high density lipoprotein-associated serum paraoxonase-1 (PON1) is essential for PON1-mediated inhibition of low density lipoprotein oxidation and stimulation of macrophage cholesterol efflux. *The Journal of biological chemistry* 2006, 281, 7657-7665

Rosenblat, M.; Vaya, J.; Shih, D.; Aviram, M., Paraoxonase 1 (PON1) enhances HDL-mediated macrophage cholesterol efflux via the ABCA1 transporter in association with increased HDL binding to the cells: a possible role for lysophosphatidylcholine. *Atherosclerosis* 2005, 179, 69-77

Rozenberg, O.; Rosenblat, M.; Coleman, R.; Shih, D. M.; Aviram, M., Paraoxonase (PON1) deficiency is associated with increased macrophage oxidative stress: studies in PON1-knockout mice. *Free radical biology & medicine* 2003, 34, 774-784

Rozenberg, O.; Shih, D. M.; Aviram, M., Human serum paraoxonase 1 decreases macrophage cholesterol biosynthesis: possible role for its phospholipase-A2-like activity and lysophosphatidylcholine formation. *Arteriosclerosis, thrombosis, and vascular biology* 2003, 23, 461-467

Santos-Gallego, C. G., HDL: Quality or quantity? *Atherosclerosis* 2015, 243, 121-123

Sattler, K.; Graler, M.; Keul, P.; Weske, S.; Reimann, C. M.; Jindrova, H.; Kleinbongard, P.; Sabbadini, R.; Brocker-Preuss, M.; Erbel, R.; Heusch, G.; Levkau, B., Defects of high-density lipoproteins in coronary artery disease caused by low Sphingosine-1-phosphate content: correction by sphingosine-1-phosphate-loading. *Journal of the American College of Cardiology* 2015, 66, 1470-1485

Sattler, K.; Levkau, B., Sphingosine-1-phosphate as a mediator of high-density lipoprotein effects in cardiovascular protection. *Cardiovascular research* 2009, 82, 201-11

Shih, D. M.; Welch, C.; Lusis, A. J., New insights into atherosclerosis from studies with mouse models. *Molecular medicine today* 1995, 1, 364-372

Shih, D. M.; Xia, Y. R.; Wang, X. P.; Miller, E.; Castellani, L. W.; Subbanagounder, G.; Cheroutre, H.; Faull, K. F.; Berliner, J. A.; Witztum, J. L.; Lusis, A. J., Combined serum paraoxonase knockout/apolipoprotein E knockout mice exhibit increased lipoprotein oxidation and atherosclerosis. *The Journal of biological chemistry* 2000, 275, 17527-17535

Sun, Y.; Zhang, H.; Sun, Y.; Zhang, Y.; Liu, H.; Cheng, J.; Bi, S.; H., Z., Study of interaction between protein and main active components in *Citrus aurantium* L. by optical spectroscopy. *Journal of Luminescence* 2010, 130, 270-279

Tang, W. H.; Hartiala, J.; Fan, Y.; Wu, Y.; Stewart, A. F.; Erdmann, J.; Kathiresan, S.; Consortium, C. A.; Roberts, R.; McPherson, R.; Allayee, H.; Hazen, S. L., Clinical and genetic association of serum paraoxonase and arylesterase activities with cardiovascular risk. *Arteriosclerosis, thrombosis, and vascular biology* 2012, 32, 2803-2812

Tavori, H.; Aviram, M.; Khatib, S.; Musa, R.; Mannheim, D.; Karmeli, R.; Vaya, J., Human carotid lesion linoleic acid hydroperoxide inhibits paraoxonase 1 (PON1) activity via reaction with PON1 free sulfhydryl cysteine 284. *Free radical biology & medicine* 2011a, 50, 148-156

Tavori, H.; Aviram, M.; Khatib, S.; Musa, R.; Mannheim, D.; Karmeli, R.; Vaya, J., Paraoxonase 1 protects macrophages from atherogenicity of a specific triglyceride isolated from human carotid lesion. *Free radical biology & medicine* 2011b, 51, 234-242

Tavori, H.; Aviram, M.; Khatib, S.; Musa, R.; Nitecki, S.; Hoffman, A.; Vaya, J., Human carotid atherosclerotic plaque increases oxidative state of macrophages and low-density lipoproteins, whereas paraoxonase 1 (PON1) decreases such atherogenic effects. *Free radical biology & medicine* 2009, 46, 607-615

Tavori, H.; Khatib, S.; Aviram, M.; Vaya, J., Characterization of the PON1 active site using modeling simulation, in relation to PON1 lactonase activity. *Bioorganic & medicinal chemistry* 2008, 16, 7504-7509

Yuhanna, I. S.; Zhu, Y.; Cox, B. E.; Hahner, L. D.; Osborne-Lawrence, S.; Lu, P.; Marcel, Y. L.; Anderson, R. G.; Mendelsohn, M. E.; Hobbs, H. H.; Shaul, P. W., High-density lipoprotein binding to scavenger receptor-BI activates endothelial nitric oxide synthase. *Nature medicine* 2001, 7, 853-857

Zakiev, E.; Feng, M.; Sukhorukov, V.; Kontush, A., HDL-Targeting Therapeutics: Past, Present and Future. *Current pharmaceutical design* 2017, 23, 1207-1215

Zheng, C.; Aikawa, M., High-density lipoproteins: from function to therapy. *Journal of the American College of Cardiology* 2012, 60, 2380-2383

The invention claimed is:

1. A compound including any pharmaceutically acceptable salt thereof, said compound is represented by formula I:

$$R_1-C(O)-R_2-R_3-COOH$$

wherein $R_1$ is ($C_{15}$-$C_{21}$)alkyl, ($C_{15}$-$C_{21}$)alkenyl, or ($C_{15}$-$C_{21}$)alkynyl;

$R_2$ is —NH—$CH_2$—$CHR_4$—$CH_2$—O—, —O—, or —NH—;

$R_3$ is —$CH_2$—CH($N^+(R_5)_3$)— or —$(CH_2)_2$—CH($N^+(R_5)_3$)—, and optionally further substituted with one or more —OH groups;

$R_4$ is —OH, —O—C(O)—$R_6$, or —NH—C(O)—$R_6$;
$R_5$ each independently is ($C_1$-$C_8$)alkyl; and
$R_6$ is ($C_{15}$-$C_{21}$)alkyl, ($C_{15}$-$C_{21}$)alkenyl, or ($C_{15}$-$C_{21}$)alkynyl,
if $R_2$, is —NH— and $R_1$ is selected from heptadecyl, and pentadecyl, then $R_5$ each independently is ethyl, n-propyl, or isopropyl.

2. The compound of claim 1, wherein $R_1$ is ($C_{15}$-$C_{21}$)alkyl, or ($C_{15}$-$C_{21}$)alkenyl.

3. The compound of claim 1, wherein $R_1$ is $CH_3$—$(CH_2)_{14}$—, $CH_3$—$(CH_2)_7$—CH=CH—$(CH_2)_7$—, $CH_3$—$(CH_2)_4$—(CH=CH—$CH_2)_2$—$(CH_2)_6$—, $CH_3$—($CH_2$—CH=CH$)_3$—$(CH_2)_7$—, $CH_3$—$(CH_2)_4$—(CH=CH—$CH_2)_4$—$(CH_2)_2$—, $CH_3$—($CH_2$—CH=CH$)_5$—$(CH_2)_3$—, or $CH_3$—($CH_2$—CH=CH$)_6$—$(CH_2)_2$—.

4. The compound of claim 1, wherein:
$R_1$ is a linear ($C_{15}$)alkyl, ($C_{17}$)alkenyl, ($C_{19}$)alkenyl, or ($C_{21}$)alkenyl; and
$R_2$ is —NH—$CH_2$—CHOH—$CH_2$—O—, —O—, or —NH—.

5. A pharmaceutical composition comprising (i) said compound of claim 1, including any pharmaceutically acceptable salt and any solvate thereof; and (ii) a pharmaceutically acceptable carrier.

6. The compound of claim 1, wherein said compound is

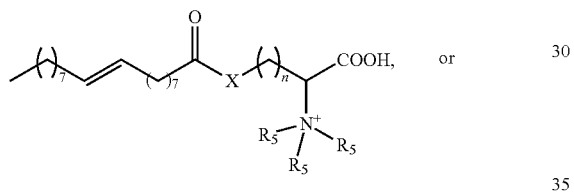

wherein R5 is methyl, n is 2; and wherein X is NH.

7. A compound including any pharmaceutically acceptable salt thereof, said compound is represented by formula I:

$R_1$—C(O)—$R_2$—$R_3$—COOH wherein
$R_1$ is selected from the group consisting of ($C_{15}$-$C_{21}$)alkyl, ($C_{15}$-$C_{21}$)alkenyl, and ($C_{15}$-$C_{21}$)alkynyl;
$R_2$ is —NH—$CH_2$—$CHR_4$—$CH_2$—O—, —O—, or —NH—;

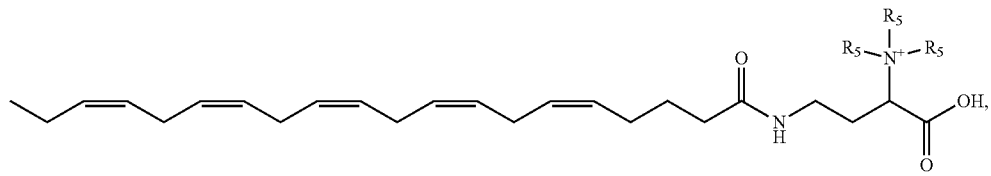

$R_3$ is —$CH_2$—CH($N^+(R_5)_3$)— or —$(CH_2)_2$—CH($N^+(R_5)_3$)—, and optionally further substituted with one or more —OH groups;
$R_4$ is —OH, —O—C(O)—$R_6$, or —NH—C(O)—$R_6$;
$R_5$ each independently is ($C_1$-$C_4$)alkyl; and
$R_6$ is ($C_{15}$-$C_{21}$)alkyl, ($C_{15}$-$C_{21}$)alkenyl, or ($C_{15}$-$C_{21}$)alkynyl,
if $R_2$, is —NH— and $R_1$ is selected from heptadecyl, and pentadecyl, then $R_5$ each independently is ethyl, n-propyl, or isopropyl.

* * * * *